United States Patent [19]

Dunn et al.

[11] Patent Number: 4,871,559
[45] Date of Patent: Oct. 3, 1989

[54] METHODS FOR PRESERVATION OF FOODSTUFFS

[75] Inventors: Joseph E. Dunn, Rancho La Costa; R. Wayne Clark, Del Mar; John F. Asmus, LaJolla; Jay S. Pearlman, Rancho Palos Verde, all of Calif.; Keith Boyer, Los Alamos, N. Mex.; Fraincois Painchaud, Charlesbourg, Canada; Gunter A. Hofmann, San Diego, Calif.

[73] Assignee: Maxwell Laboratories, Inc., San Diego, Calif.

[21] Appl. No.: 187,281

[22] Filed: Apr. 28, 1988

Related U.S. Application Data

[63] Continuation-in-part of Ser. No. 794,573, Nov. 4, 1985, abandoned, which is a continuation-in-part of Ser. No. 731,665, May 7, 1985, abandoned, which is a continuation-in-part of Ser. No. 555,383, Nov. 23, 1983, abandoned, which is a continuation-in-part of Ser. No. 703,289, Feb. 20, 1985, abandoned, which is a continuation-in-part of Ser. No. 930,646, Nov. 13, 1986, abandoned.

[51] Int. Cl.[4] .......................... A23L 3/00; A23L 3/28; A61L 2/00
[52] U.S. Cl. ..................................... 426/248; 426/407; 426/410; 426/521; 422/24
[58] Field of Search ............... 426/237, 238, 240, 248, 426/521, 407, 410, 522; 422/24, 22, 23

[56] References Cited

U.S. PATENT DOCUMENTS

| | | | |
|---|---|---|---|
| 2,072,416 | 3/1937 | Berndt et al. | 99/13 |
| 2,072,417 | 3/1937 | Berndt et al. | 99/13 |
| 2,482,507 | 9/1949 | Rentschler et al. | 426/248 |
| 2,930,706 | 3/1960 | Moulton . | |
| 3,814,680 | 5/1971 | Wood . | |
| 3,817,703 | 9/1971 | Atwood . | |
| 3,955,921 | 5/1976 | Tensmeyer . | |
| 4,042,325 | 8/1977 | Tensmeyer . | |
| 4,265,747 | 5/1981 | Copa et al. . | |
| 4,391,080 | 7/1983 | Brody et al. . | |
| 4,424,188 | 1/1984 | Di Geronimo | 422/24 |
| 4,464,336 | 8/1984 | Hiramota . | |

FOREIGN PATENT DOCUMENTS

| | | |
|---|---|---|
| 1052513 | 12/1966 | United Kingdom . |
| 1346521 | 2/1974 | United Kingdom . |
| 1448411 | 9/1976 | United Kingdom . |
| 1548997 | 7/1979 | United Kingdom . |
| 1581998 | 12/1980 | United Kingdom . |

OTHER PUBLICATIONS

Rentschler et al., "Bactericidal Effect of Ultraviolet Radiation", J. of Bacteriology, vol. 41, No. 6, Jun. 1941.
Johnson, T., "Flashblast–The Light That Cleans", Popular Science, Jul. 1982, pp. 82–84.

*Primary Examiner*—Marianne Cintins
*Attorney, Agent, or Firm*—Fitch, Even, Tabin & Flannery

[57] ABSTRACT

Methods and apparatus for food product preservation by inactivation of microorganisms and/or enzymes by applying pulses of very intense, very short duration pulses of light in the visible and near visible frequencies to the surface of food products to be preserved. Also disclosed are packaging methods and apparatus utilizing such intense, short pulses of polychromatic, incoherent light.

27 Claims, 24 Drawing Sheets

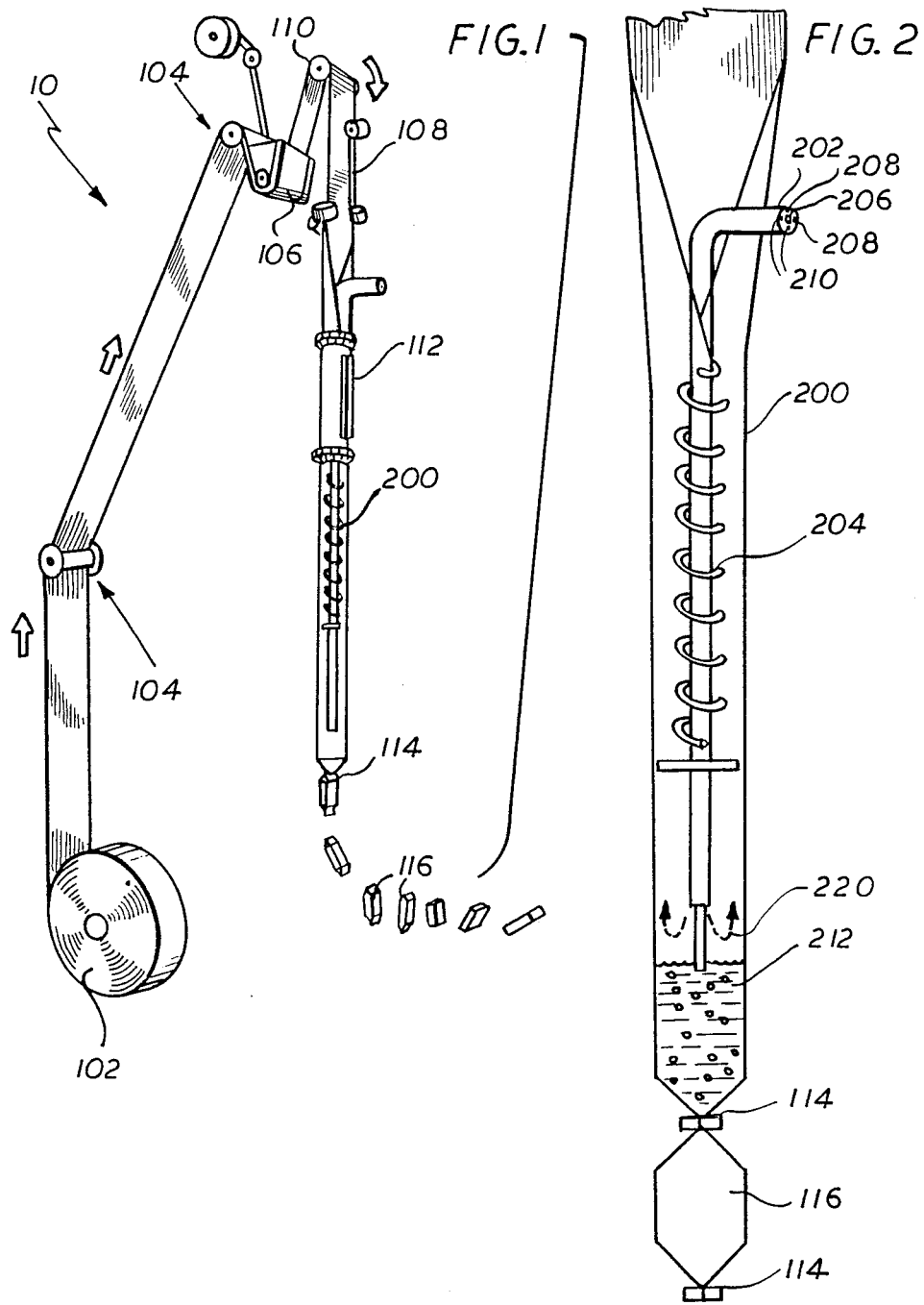

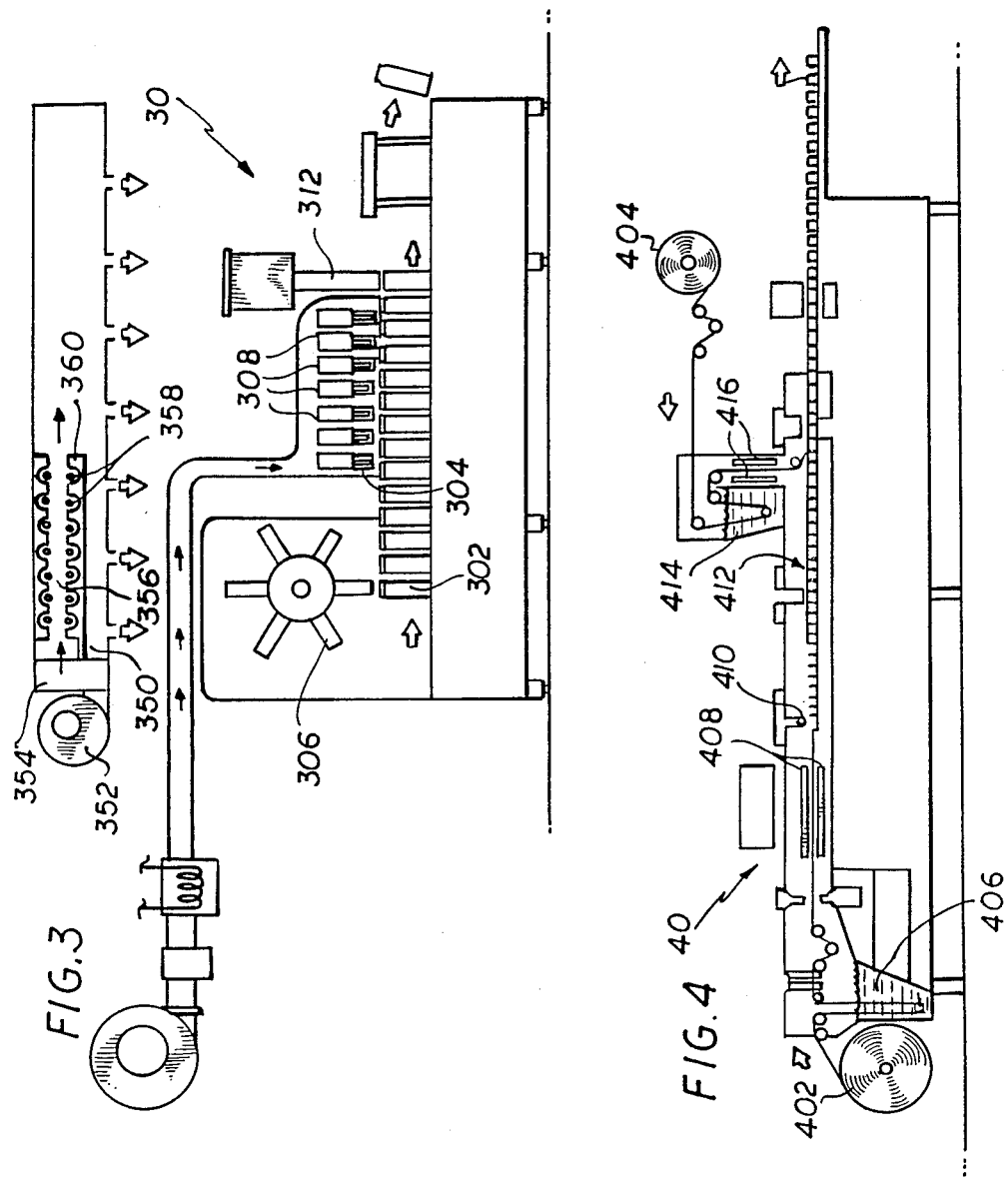

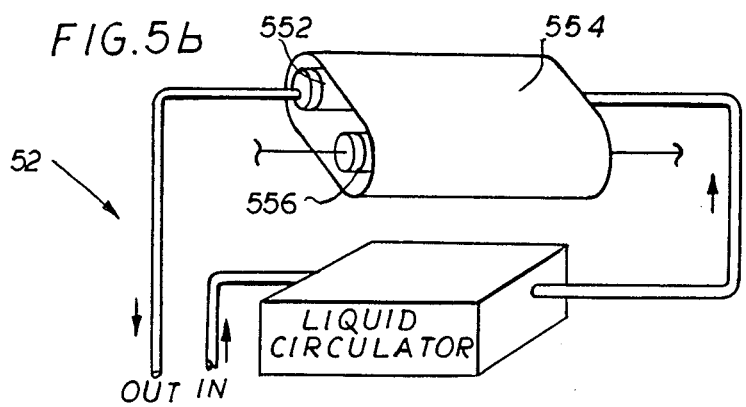
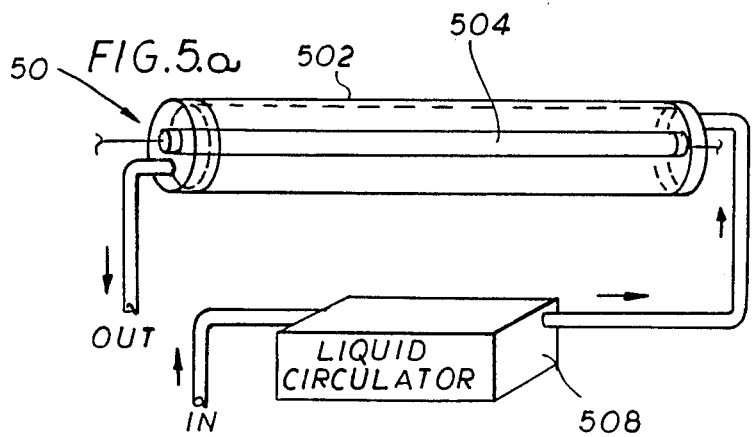
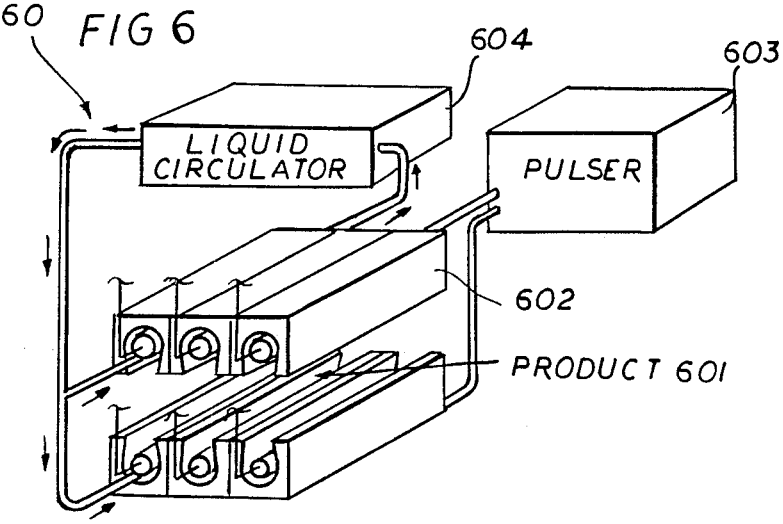

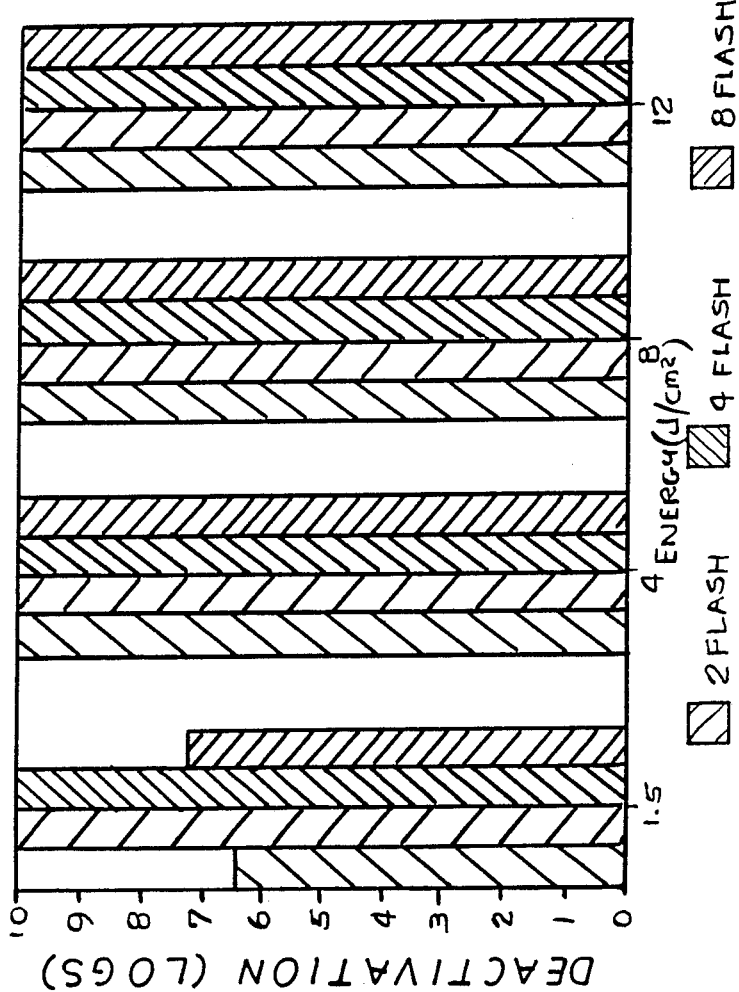

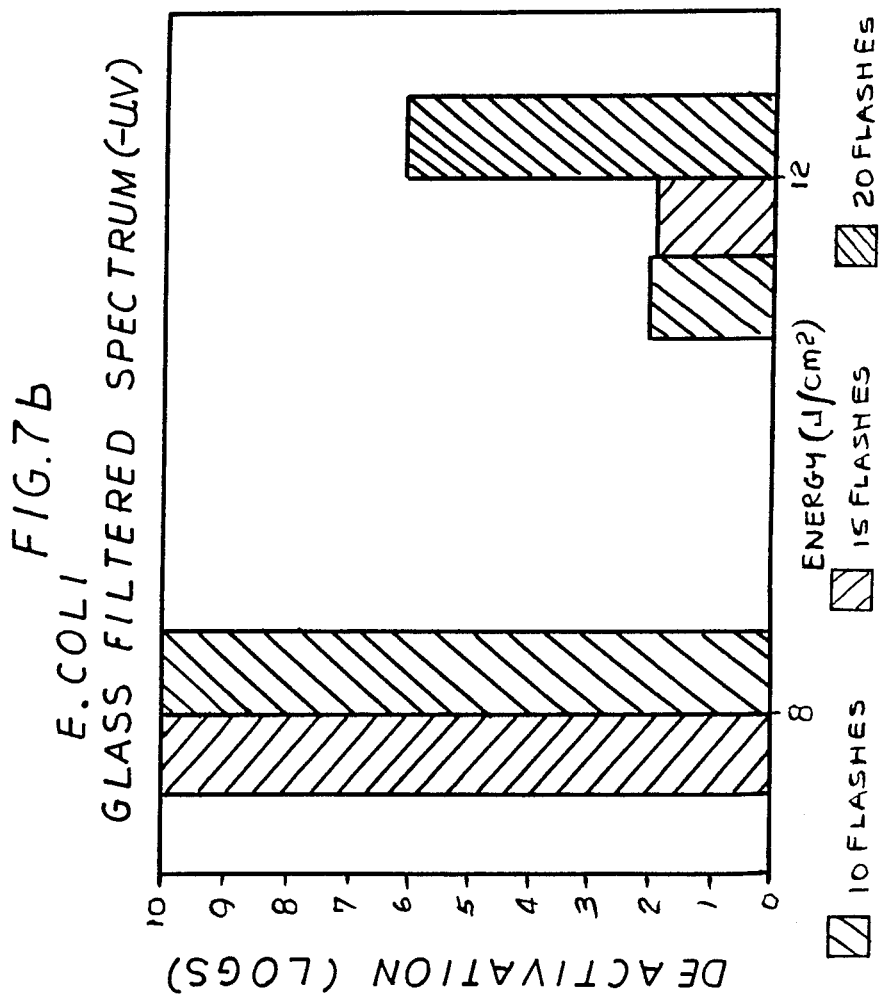

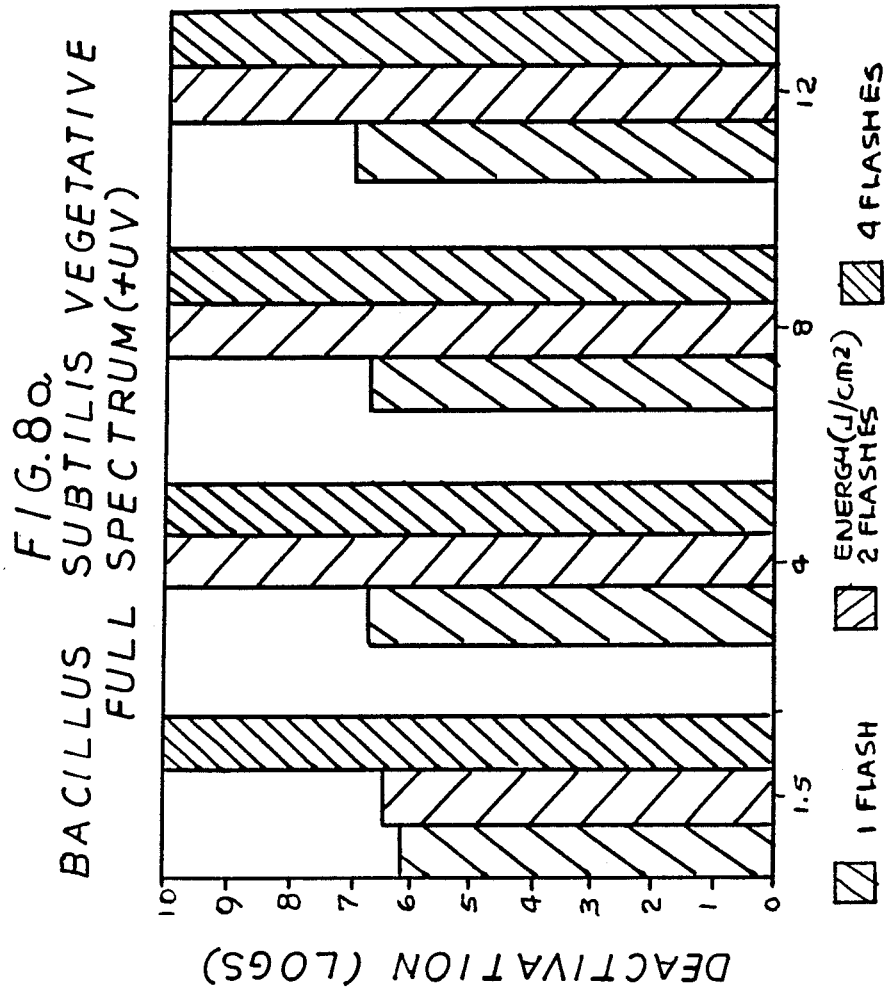

BACILLUS SUBTILIS VEGETATIVE
GLASS FILTERED SPECTRUM (–UV)

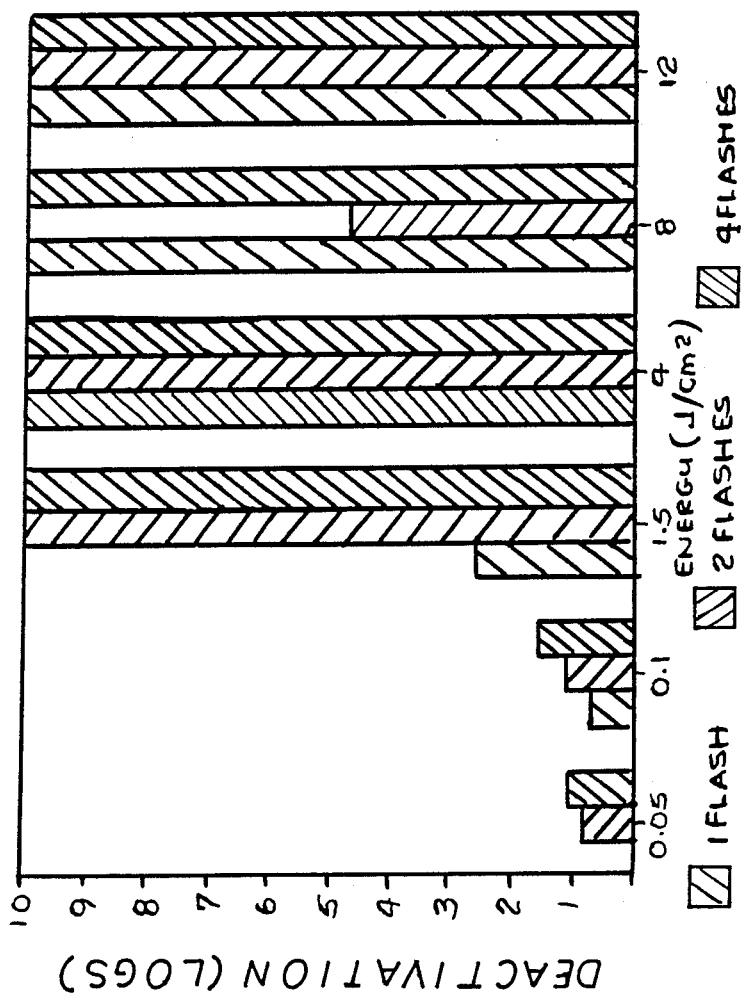

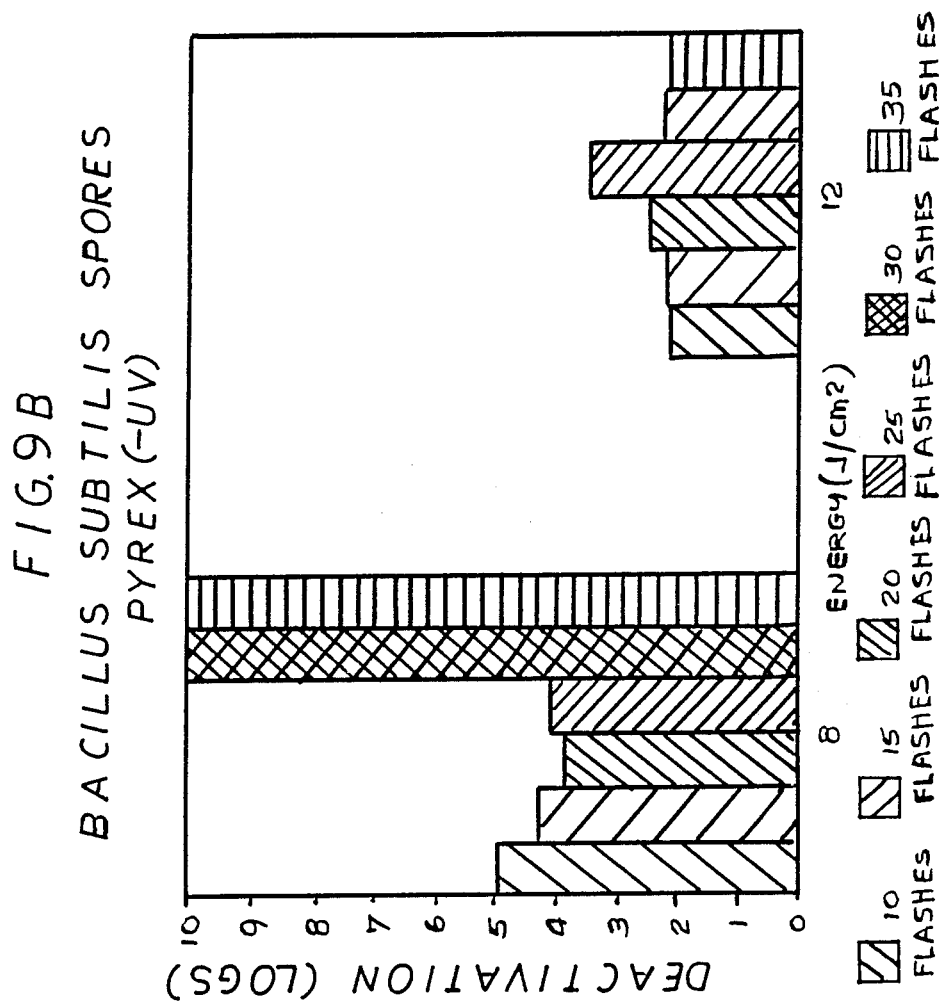

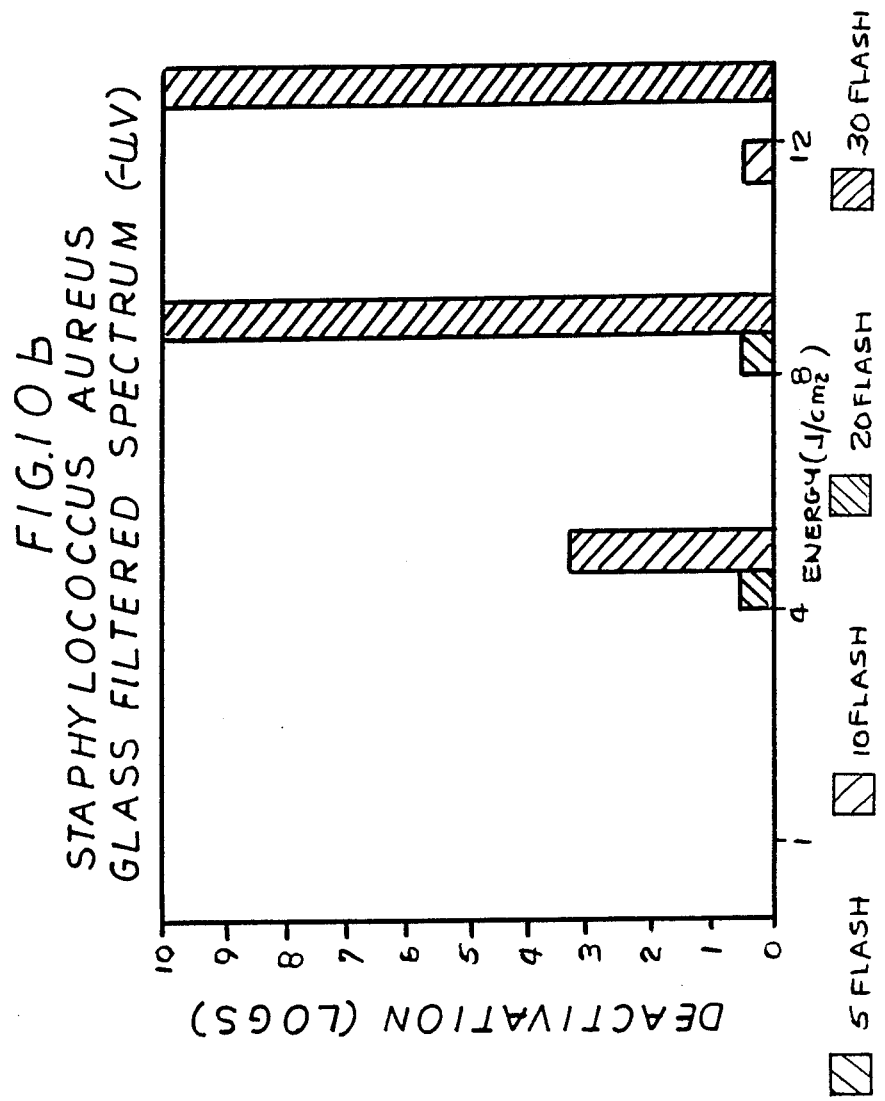

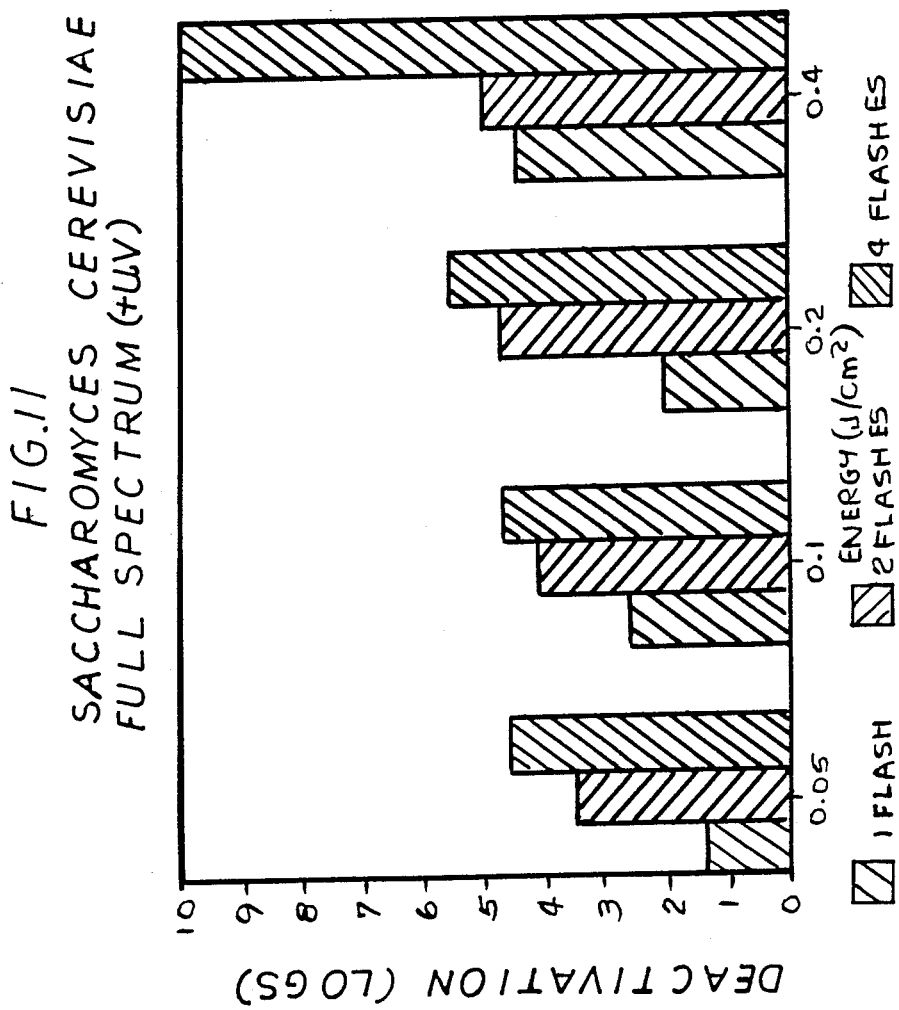

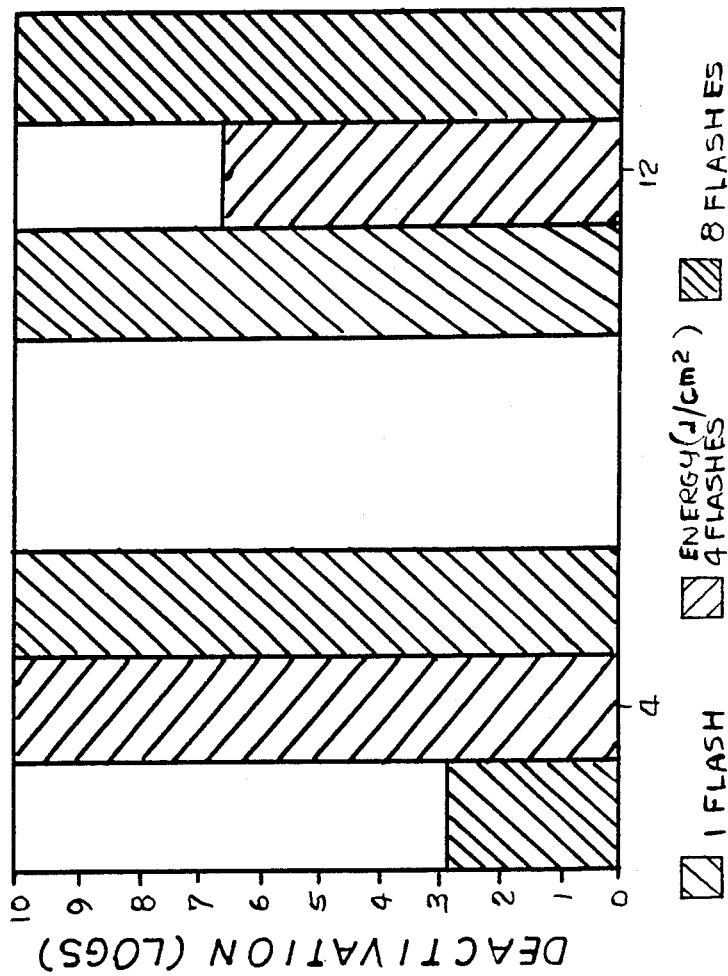

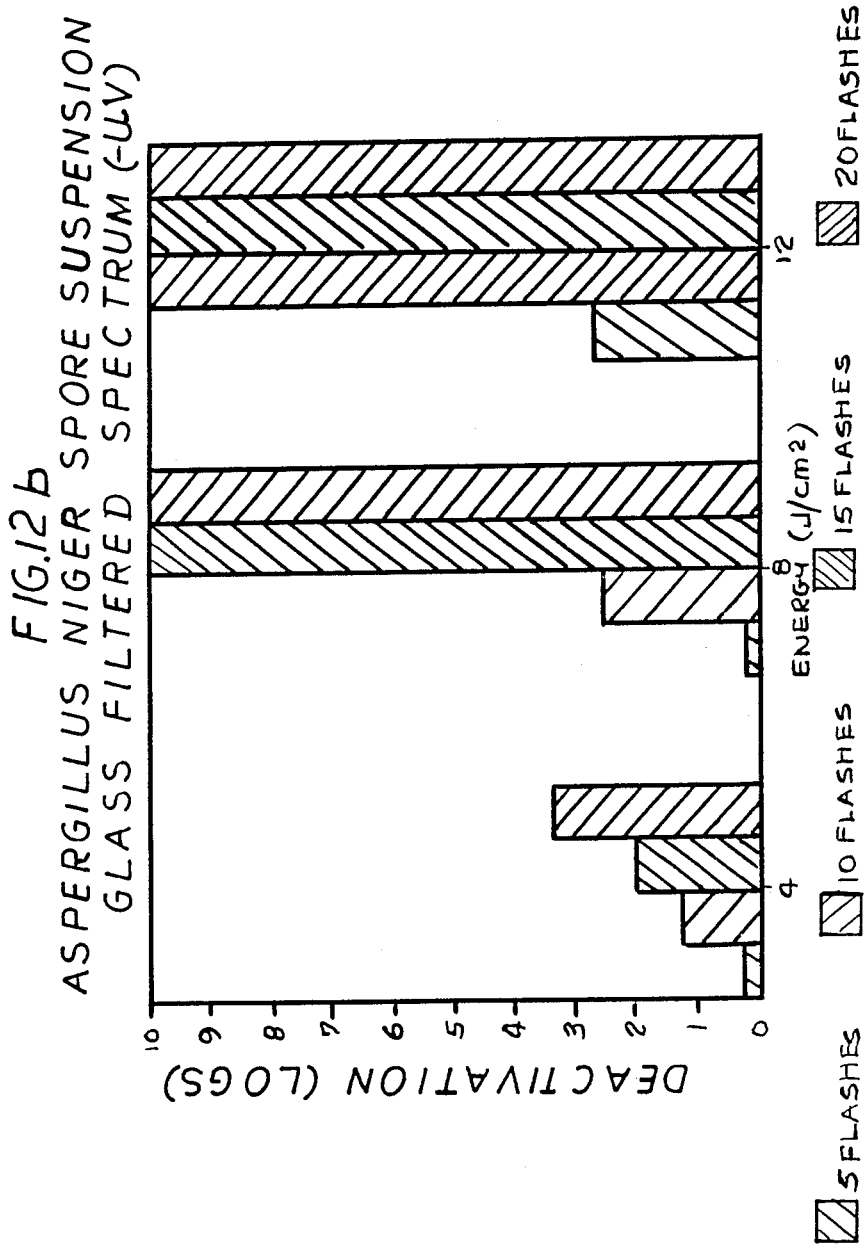
FIG. 12b ASPERGILLUS NIGER SPORE SUSPENSION GLASS FILTERED SPECTRUM (-

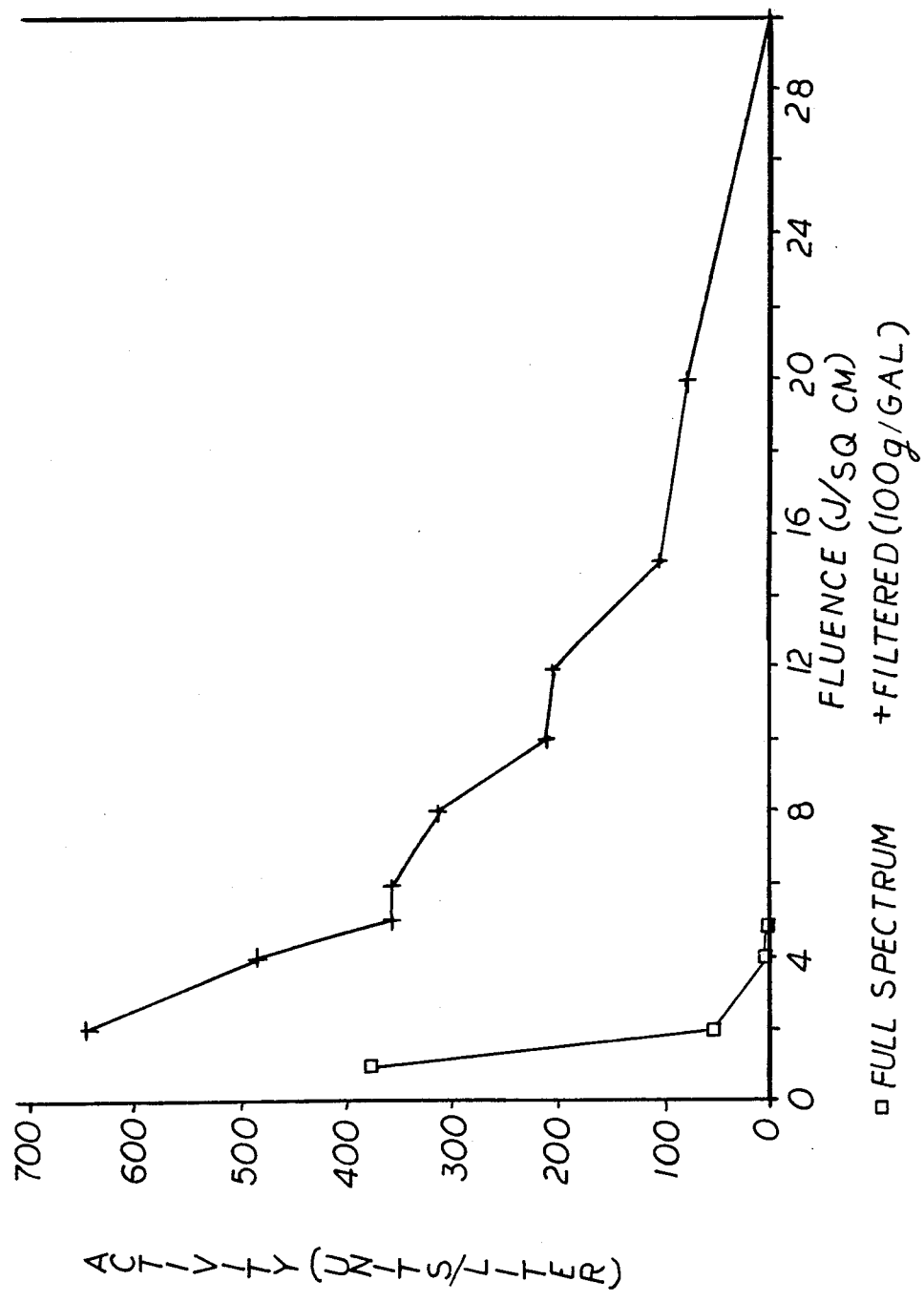

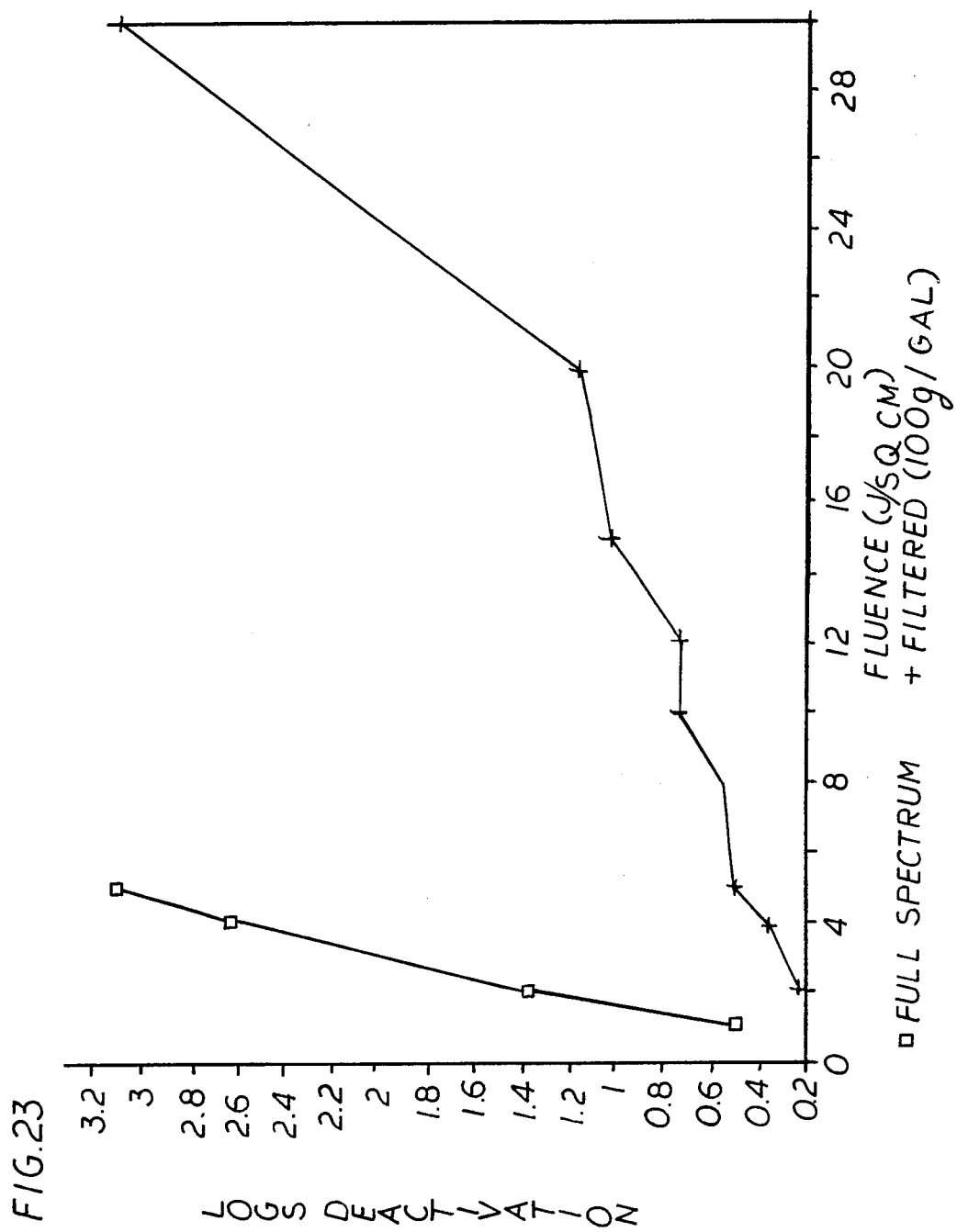

METHODS FOR PRESERVATION OF FOODSTUFFS

This application is a continuation-in-part of application Ser. No. 794,573 filed Nov. 4, 1985, now abandoned; application Ser. No. 731,665 filed May 7, 1985, now abandoned; application Ser. No. 555,383 filed Nov. 23, 1983, now abandoned; and U. S. application Ser. No. 703,289 filed Feb. 20, 1985, now abandoned; and application Ser. No. 930,646 filed Nov. 13, 1986, now abandoned; which are incorporated herein by reference.

The present invention relates to methods and apparatus for food preservation and packaging, and more particularly, is directed to food preservation and packaging methods and apparatus which utilize intense incoherent pulsed light.

BACKGROUND OF THE INVENTION

Substantial technical effort has been directed to extend the storage time for foodstuffs and other microbiologically labile products and to preserve these products against microbiological spoilage. Such efforts have involved both the treatment of products and the development of packaging techniques for preservation.

The present invention addresses the particular need which exists for methods and apparatus for sterilizing or reducing the microbiological burden on the surfaces of or within foodstuffs and other products, which may be utilized to reduce or eliminate the need for chemical preservatives. For example, baked goods such as bread may accumulate microorganisms, such as mold spores, from the air after they are baked but before they cool sufficiently to be packaged. Any substantial reheating of the baked goods would excessively dry the products and new methods for surface sterilization of such foodstuffs would be desirable. Food products may also be subject to enzymatic degradation, which limits shelf life of the food product. Enzymatic degradation is particularly rapid and evident for example in the browning of freshly cut potatoes and apples, but has adverse effects in a great variety of foods, alone, or in combination with microbially caused deterioration. For example, foods such as fresh fish have a relatively limited storage time before being subject to microbial and/or enzymatic spoilage, which limits the distribution and marketing of fresh fish products. Methods and apparatus suitable for extending the shelf life of perishable foods such as fresh fish, poultry, beef and pork would be desirable.

Also, many products, for example some juices, are now processed through the use of heat under conditions which, in order to produce the desired reduction in biological activity, cause a degradation of the taste and palatability of the treated food product. Methods and apparatus for reducing or eliminating biological activity without such degradative heating would be desirable for providing taste and palatability benefits which would increase the consumer interest and hence market for products so treated.

Significant research and development effort has recently been directed to aseptic packaging technology for packaging of sterilized food products (including high and low acid foods) in sterile packaging materials, in order to provide preserved foodstuffs having an extended shelf life. However, such methods and apparatus may have various disadvantages such as requiring the extensive use of chemical disinfectants which may leave residual chemical products on the packaging material or foodstuff. New methods and apparatus for sterilizing food product packaging material and for aseptic packaging would be desirable.

The photobiological effects of light, including visible light (380–780 nm), near ultraviolet light (300–380 nm) and far ultraviolet light (190–300 nm), have been studied for many years, for example, as reported in Jagger, J., "Introduction to Research in Ultraviolet Photobiology", Prentice Hall, Inc., 1967, and efforts have been made to employ light to sterilize food products or containers for food products. U.S. Pat. No. 2,072,417 describes illuminating substances, e.g., milk, with active rays, such as UV rays. U.S. Pat. No. 3,817,703 describes sterilization of light-transmissive material using pulsed laser light. U.S. Pat. No. 3,941,670 describes a method of sterilizing materials, including foodstuffs, by exposing the material to laser illumination to inactivate microorganisms. However, such methods have various deficiencies, such as limited throughput capacity, limited effectiveness, adverse food effects, inefficient energy conversion (electrical to light) and economic disadvantages.

Accordingly, it is an object of the present invention to provide new methods and apparatus for the reduction of the biological burden of food products, liquids, equipment, devices and atmospheres. It is a further object to provide new methods and apparatus for preserving foodstuffs and for packaging of foodstuffs, particularly including improved aseptic packaging processes and apparatus.

These and other objects of the invention will become more apparent from the following detailed description and the accompanying drawings, of which:

FIG. 1 is a schematic illustration of an embodiment of an aseptic packaging machine which continuously forms and fills a continuous packaging film and sterilizes the film by high intensity incoherent light pulses to provide aseptically packaged food products;

FIG. 2 is a perspective view, partially broken away, of the high intensity incoherent pulsed light filling and sterilization assembly of the aseptic packaging apparatus of FIG. 1;

FIG. 3 is a schematic illustration of another embodiment of a packaging system which is adapted to aseptically package a sterilized food product in preformed containers which are sterilized by means of high intensity incoherent light pulses;

FIG. 4 is a schematic side view of an embodiment of an aseptic packaging apparatus which forms and sterilizes containers from rolls of thermoplastic and lid materials;

FIG. 5a is a schematic view of an embodiment of pulsed light processing apparatus which treats pumpable products flowing longitudinally through a jacket surrounding an elongated, incoherent pulsed light source;

FIG. 5b is a schematic view of another embodiment of pulsed light processing apparatus which treats pumpable fluids flowing in a direction parallel to one or more elongated incoherent light sources;

FIG. 6 is a schematic view of an embodiment of a processing apparatus for treating products passing through an intense incoherent pulsed light treatment station;

FIG. 7a and 7b are graphic representations of *E. coli* deactivation on culture media by means of high intensity incoherent light pulses;

FIGS. 8a and 8b are graphic representations of *Bacillus subtilis* (vegetative) deactivation on culture media by means of high intensity incoherent light pulses;

FIGS. 9a and 9b are graphic representations of *Bacillus subtilis* (spores) deactivation on culture media by means of high intensity incoherent light pulses;

FIGS. 10a and 10b are graphic representations of *Staphylococcus aureus* deactivation on culture media by means of high intensity incoherent light pulses; FIG. 11 is a graphic representation of *Saccharomyces cerevisiae* deactivation on culture media by means of high intensity incoherent light pulses;

FIGS. 12a and 12b are graphic representation of *Aspergillus niger* spore suspension deactivation on potato dextrose agar culture media supplemented with rose bengal, by means of high intensity incoherent light pulses;

Figure 15:
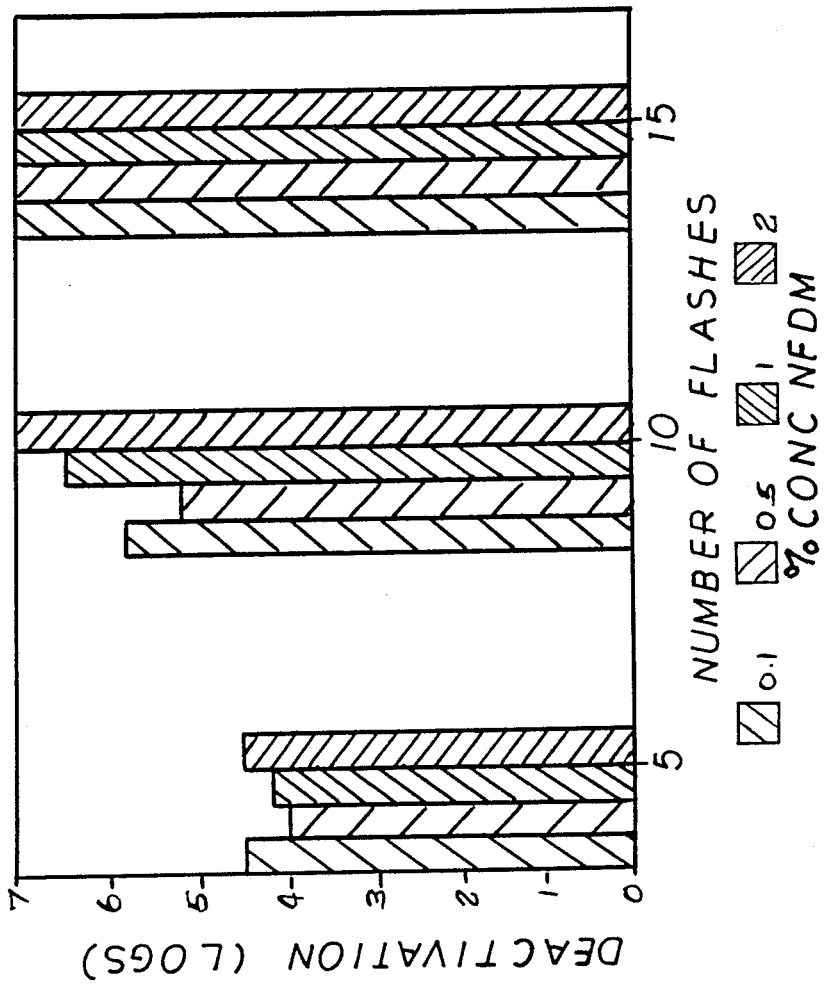
Figure 16:
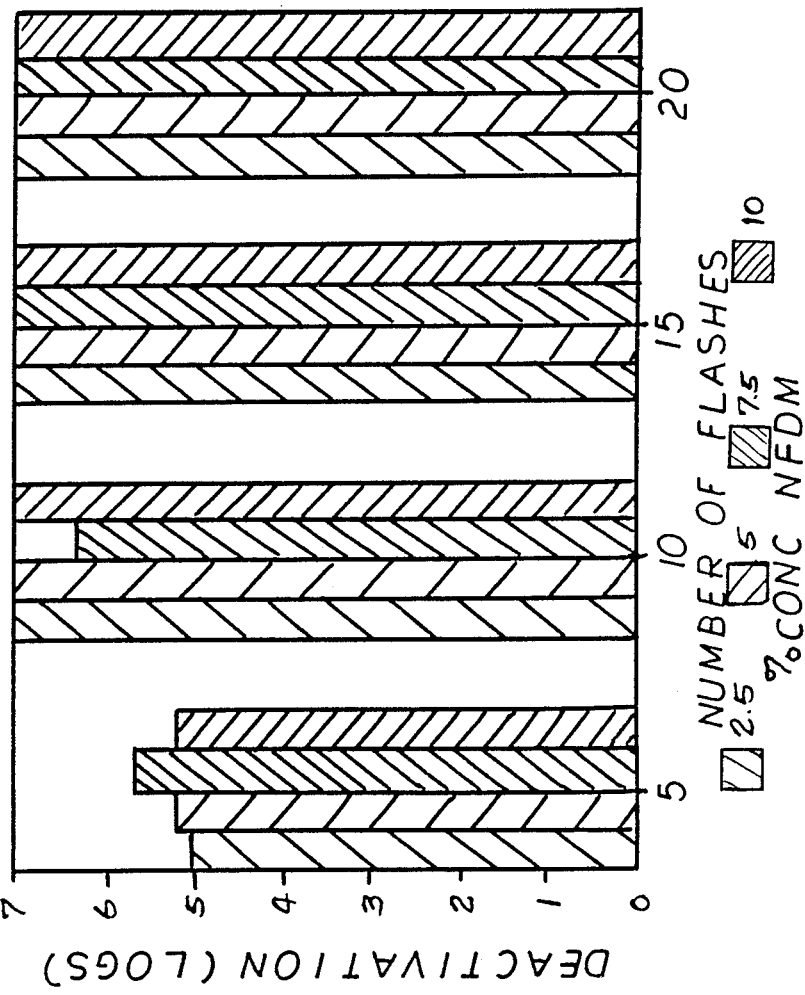
Figure 17:
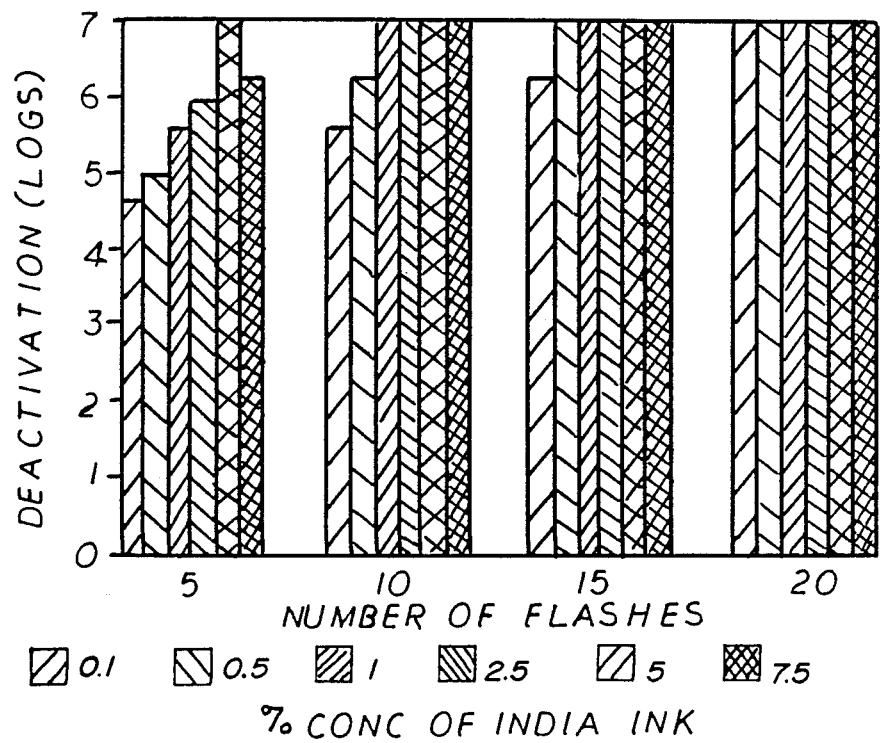
Figure 18:
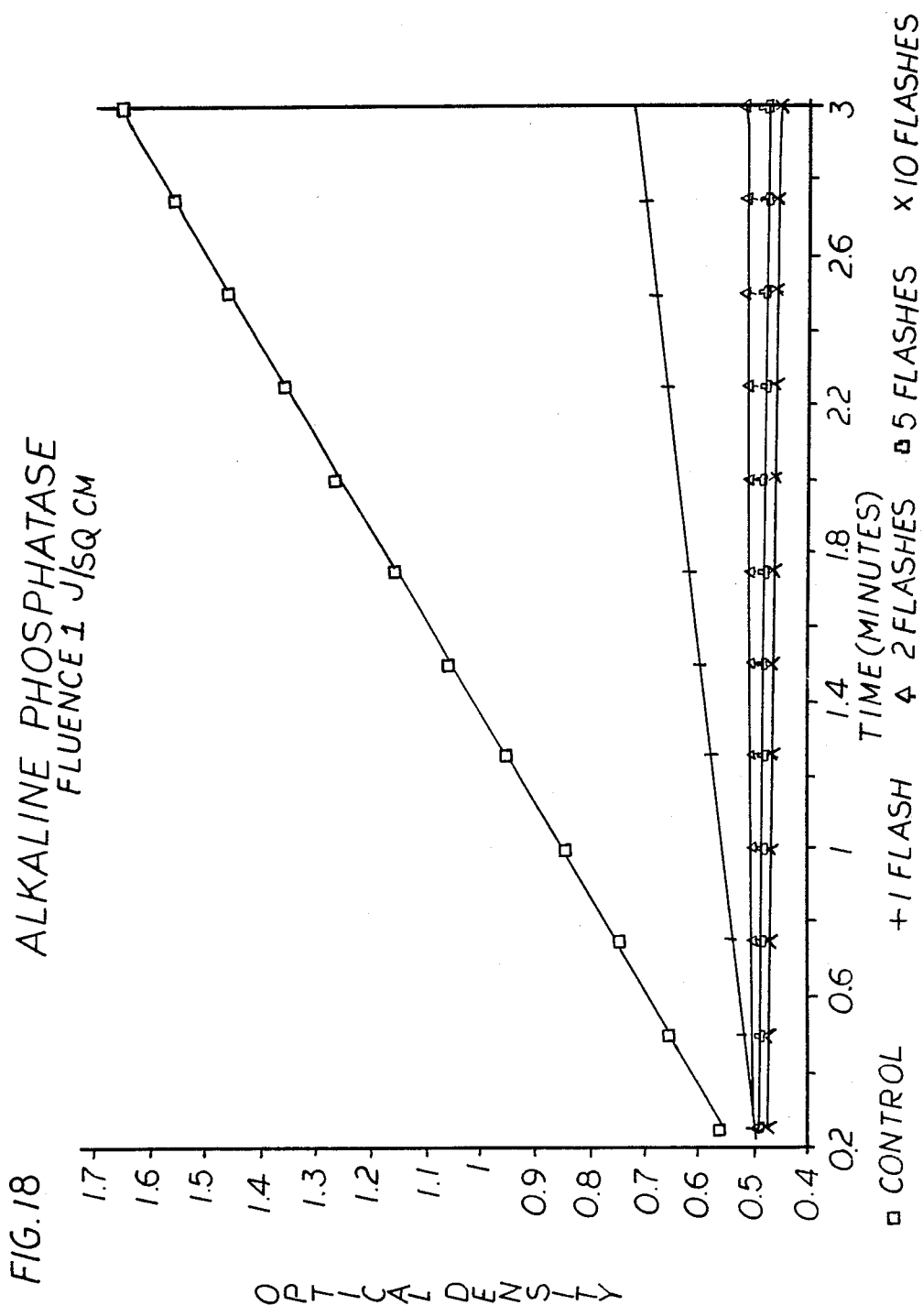
Figure 19:
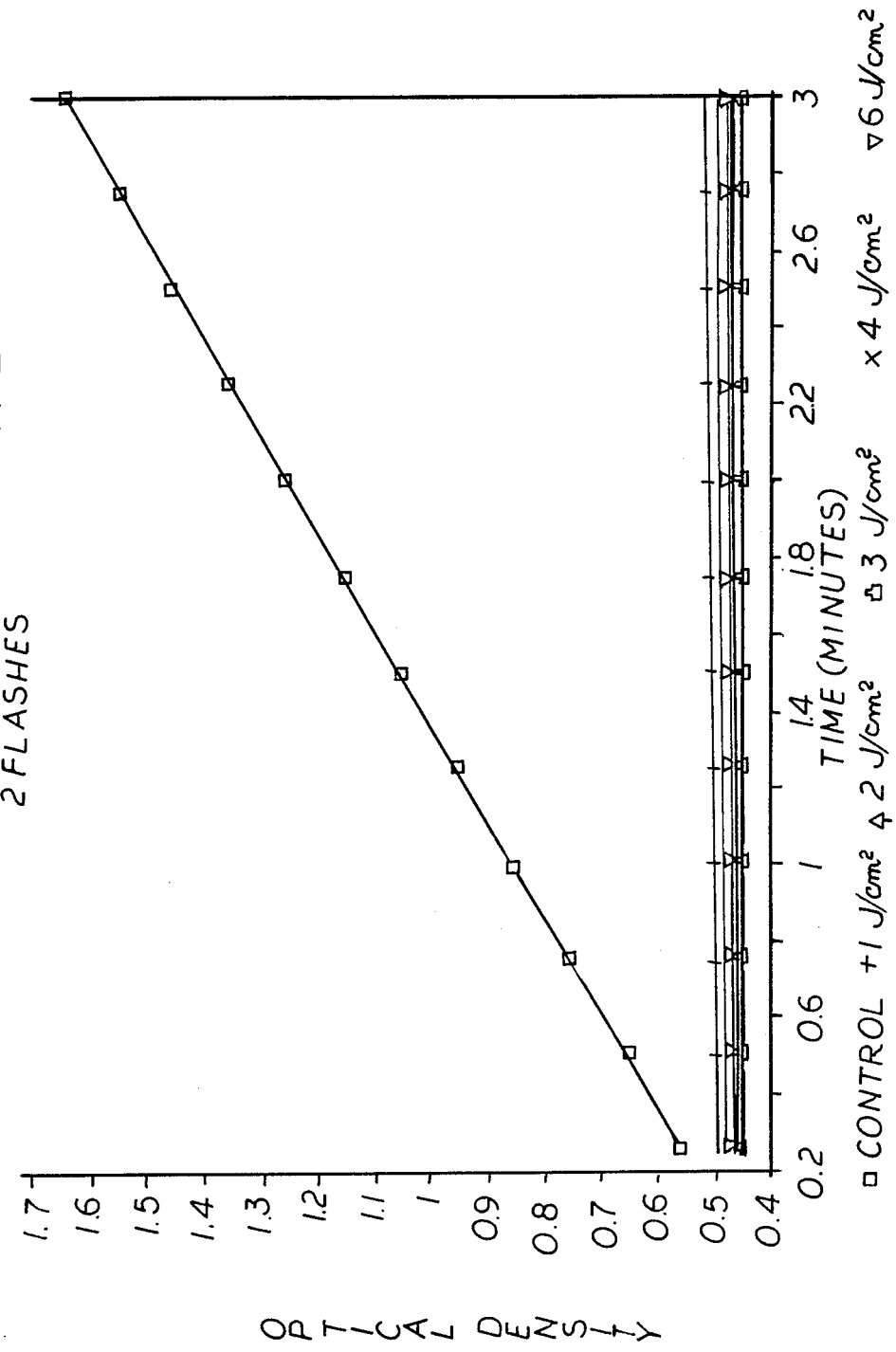
Figure 20:
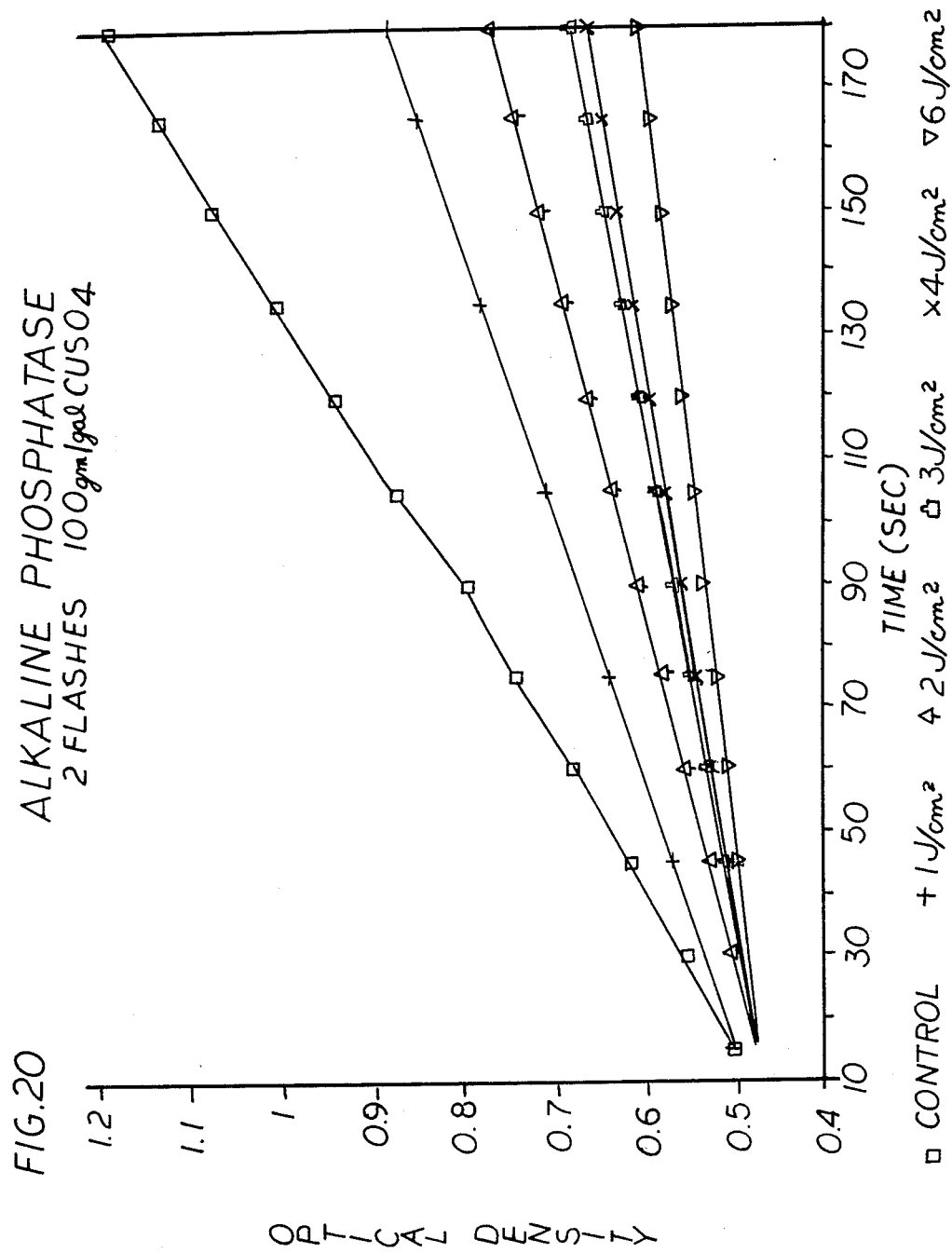
Figure 21:
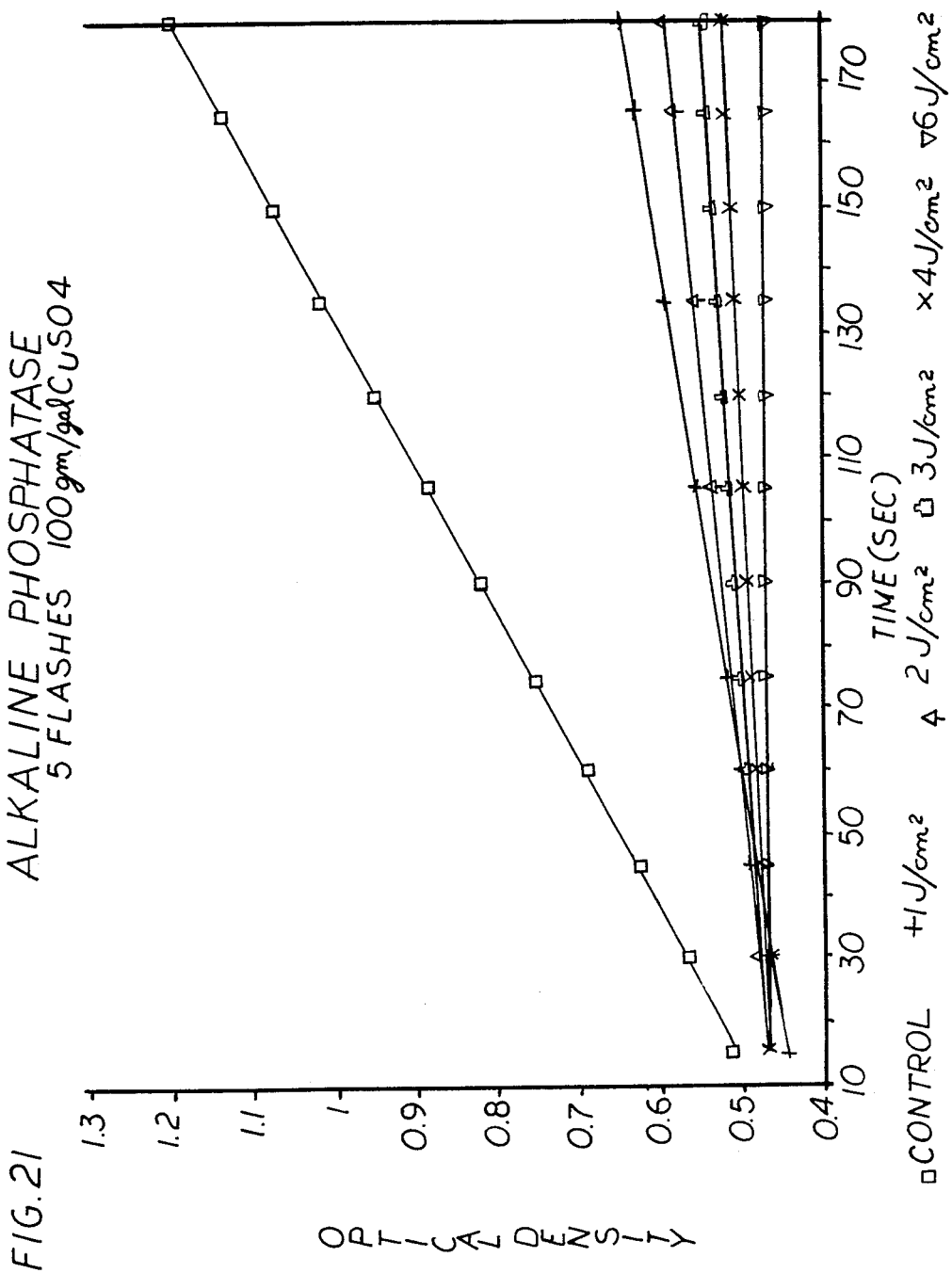

FIGS. 15 and 16 are graphic representations of *E. coli* deactivation using nonfat dry milk in the culture medium to increase its relative absorption of high intensity incoherent light pulses from which UV light has been filtered, FIG. 17 is a graphic representation of *E. coli* deactivation using india ink in the culture medium to increase its relative absorption of high intensity incoherent light pulses from which UV light has been filtered, FIG. 18 is a graphical representation of alkaline phosphatase activity following pulsed light treatment at a fluence of one joule per square centimeter, as a function of the number of treatment flashes, as measured by accumulation of optical density at 405 nanometers versus time to determine the hydrolysis of p-nitrophenyl phosphate to produce p-nitrophenyl, FIG. 19 is a graphical representation of alkaline phosphatase activity following pulsed light treatment using two flashes at a number of different treatment fluences, similar to FIG. 18, as measured by using optical density at 405 nanometers versus time to determine the hydrolysis of p-nitrophenyl phosphate, FIG. 20 is a graphical representation like that of FIG. 19, in which the light pulses are filtered through a copper sulfate solution to remove ultraviolet portions of the spectrum, FIG. 21 is a graphical representation like that of FIG. 20, utilizing five treatment flashes at a variety of different fluences, FIG. 22 is a graphical representation of alkaline phosphatase activity versus treatment fluence, for both full spectrum flashlamp pulsed light treatment and for pulsed light in which the ultraviolet spectrum has been removed by filtering through a copper sulfate solution, and FIG. 23 is a graphical representation of the logarithmic deactivation of alkaline phosphatase activity versus pulsed light fluence, for both full spectrum flashlamp pulsed light treatment and for pulsed light in which the ultraviolet spectrum has been removed by filtering through a copper sulfate solution.

SUMMARY OF THE INVENTION

The present invention is directed to methods and apparatus for food preservation and packaging using intense, short pulses of incoherent, broad spectrum light. In accordance with the present methods, food products may be preserved in respect to microbial and/or enzymatic degradative processes, providing significant shelf-life and stability enhancements. Application of pulses of high intensity, incoherent polychromatic light provides efficient, effective, high throughput processing and results in many practical and economic advantages. Moreover, the short duration of each pulse also permits under certain conditions, spatial localization of various of the preservative effects of the light pulses to a thin surface layer such as the surface of a food product, packaging material or medical device.

Generally, in accordance with the present invention, methods are provided for preserving foodstuffs and for inactivating microorganisms and/or enzymes on food product surfaces and packaging material surfaces, or in bulk transparent media, by exposing the media or surface to at least one pulse of incoherent light having an energy density in the range of from about 0.01 to about 50 joules per square centimeter at the surface of the food product or packaging material surface to be treated using a wavelength distribution such that at least about 70%, and preferably at least about 95% of its electromagnetic energy is distributed in a wavelength range of from 170 nanometers to 2600 nanometers, and a duration in the range of from about $1 \times 10^{-6}$ to about $1 \times 10^{-1}$ seconds, but preferably less than about 10 milliseconds. Desirably, at least about 40 percent, and typically greater than about 70 percent of the energy of the light pulses should be of continuous emission spectra. However, intense pulses from sources including significant line emission spectra may also be beneficially utilized in specific processes. Such short, intense, incoherent light pulses may be provided by pulsed, gas-filled flashlamps, spark-gap discharge apparatus, or other pulsed incoherent light sources. Pulsed, gas-filled flashlamps produce broadband light when an electrical current pulse is discharged through the flashlamp, ionizing the gas and producing an intense burst of both continuum and line emission over a broad spectral range. Such flashlamps typically employ inert gases such as Xenon or Krypton because of their high efficiencies of electrical to optical energy conversion. The use of other gases or gas mixtures and gas discharge systems is possible and may be desirable for specific applications. The application of an intense pulse of broadband light in accordance with various aspects of the present invention is believed to provide different lethal effects over a range of wavelengths, in contrast to the effect of single line emission spectrum of, for example, a low or high power continuously operating germicidal lamp.

Also in accordance with the invention, particular spectral distributions of the pulsed, high intensity incoherent light may be selected for particular purposes, by selection of the operating characteristics of the pulsed light source and/or by appropriate filtering. In this regard, for example, it is desirable for certain aseptic packaging processes that the packaging material be treated with pulses having a relatively high ultraviolet content, to minimize the total fluence necessary to achieve elimination of, or a predetermined reduction in, microorganism colony forming units (CFU). Far and near UV components of an incoherent, high intensity light pulse may be used for efficient and economic deactivation of microorganisms, microbes, enzymes or viruses through photochemical effects so as to render them reproductively or chemically inactive on the surface of, and within the near surface region of a solid foodstuff of packaging material surface, or within the bulk volume of a liquid or gas, as will be described in more detail hereinafter. Spectral distributions and light pulse intensities which utilize a photothermal mechanism, such as through photothermal chromophores within the microorganism, microbe, enzyme and/or virus, or through photothermal absorption at a surface or near a surface to be treated, are also contemplated herein. Both mechanisms may be utilized in highly efficient and effective food preservation and aseptic packaging treatment methods.

Desirably, the intensity of a particular wavelength distribution will be selected which will provide at least a reduction of initially present colony forming units at the surface to be treated (or throughout the volume of a fluid media to be treated) by a factor of at least 10 (one log reduction, base 10) and more preferably at least one thousand (three logs reduction, base 10) upon treatment with the intense pulses of light. Reduction of colony forming units by a factor of at least a million or more (six logs reduction, base 10), ranging up to complete sterilization may be provided in accordance with the present invention. The desired intensity will be less for UV-rich light pulses, and will be higher for processes which utilize a significant degree of surface heating for organism inactivation.

In addition to solid food products which may exhibit dramatic improvements in shelf life and stability as a result of enzymatic and microbial inactivation, aseptic packaging materials, fluids such as air or water, or medical supplies such as surgical instruments, may also be subjected to intense, short pulses of UV-rich polychromatic incoherent light, which may or may not utilize surface heating to effect microorganism inactivation. In accordance with such methods, at least about 5 percent, and preferably at least about 10 percent of the energy of the light pulses will be at wavelengths shorter than 300 nanometers. Such UV rich pulses may typically have relatively low total energy density, such as in the range of from about 0.01 to about 15 joules per square centimeter, and typically from about 0.1 to about 3 joules per square centimeter. A single pulse of such UV rich light having a broad spectral range may produce effective sterilization of a desired substrate, and may be absorbed by and damage with lethal effect a broad range of different chromophoric groups of microbiological cell constituents, over a broad spectral range.

For treating food product surfaces, it may be desirable to filter out portions of the polychromatic, incoherent light spectrum produced by a pulsed high intensity flashlamp(s). For example, certain preferred methods for treating food products may utilize spectral control and/or filtering to minimize the spectral fluence at wavelengths considered undesirable due to adverse effects certain bandwidths might have on foodstuff flavor or quality. For example, in accordance with various methods within the scope of the present invention, food products may be treated with intense, polychromatic incoherent light pulses having at least about 90 percent of their energy distributed between 300 and 2500 nanometers and a flash duration in the range of from about 0.001 and about 100 milliseconds at an energy density at the foodstuff surface in the range of from about 0.01 and about 20 joules per square centimeter. In addition to flashlamps, other pulsed light discharge devices producing appropriate broadband spectra and intensities may be used for the processes described herein.

Typically, food surfaces and packaging substrates may be exposed to between about 1 and about 20 pulses of high intensity, short duration incoherent light, with the use of a plurality of at least two pulses being particularly desirable. In various embodiments, the foodstuffs may be contained in a packaging material which is sufficiently transparent to the desired treatment spectrum prior to exposing its surfaces to the light pulses. In this regard, the packaging material containing the foodstuff to be treated may best transmit at least about 10% and more preferably at least about 50% of the energy of the light pulse over a predetermined treatment wavelength range less than about 320 nanometers.

In the treatment of fluids (such as air or aqueous liquids such as beverages, or water) which may contain undesirable microorganisms, intense incoherent polychromatic light pulses may be provided which have a specified energy density (as described herein) throughout the fluid volume undergoing treatment in a treatment zone. In this regard, at least a specified minimum energy level of the pulsed light should best be present throughout the treatment volume which is sufficient to produce the desired level of disinfection. Such methods may be static in a fixed treatment volume of fluid, or may be continuous in which the fluid is conducted through a treatment zone at a rate which (in conjunction with the light pulse rate) assures that the entire volume passing through the treatment zone is subjected to the prescribed minimum level of pulsed light treatment.

Various fluids such as substantially pure air and water have a high degree of transparency to a broad range of wavelengths, including the visible and UV spectral ranges, so that the treatment volumes and rates for such fluids may be relatively large. Other liquids such as clear sugar solutions, wine, etc. may have more limited transparency, which may be accommodated by the use of correspondingly smaller [e.g., thinner in the direction(s) of propagation of the light pulse] treatment volumes. It is preferred that the fluid have a transparency to UV light, such that at least half of incident light at 260 nanometers is transmitted through a 0.025 centimeter thickness of the fluid. Desirably, when treating fluid materials the fluids will be substantially free of solid, particulate materials (e.g., pure liquids or liquid mixtures, or solutions in which solids are dissolved in a liquid solvent) so that any microbial and/or enzymatic content of the fluid will be maximally subjected to the intense light field without shadowing effect. However, it will also be appreciated that solid materials such as cut, sliced or particulate foods (e.g., dried vegetables) may be conveniently treated in a fluid (e.g., water) suspension medium, preferably with multiple pulses, which may desirably be in multiple propagation directions to insure that all solid surfaces are treated.

In addition to treating fluids by providing a suitable intensity of pulsed incoherent light throughout the volume of fluid to be treated, the fluid may also be treated by providing multiple pulsed light treatment with mixing (preferably turbulent mixing) of the fluid between the individual pulses. However, while such treatment methods may reduce the microbial and/or degradative enzymatic content, they are significantly less desirable and less efficient than the whole volume treatment methods.

In accordance with various aspects of the present invention, particularly in respect to such methods in which the ultraviolet component of the pulsed light flashes is suppressed or substantially eliminated, the intensity of the pulsed light should be sufficient to heat a superficial layer of the foodstuff or packaging material having a thickness of less than 1000 microns, at least about 50° C. to a temperature of at least about 75° C. and preferably at least about 100° C. Such a very thin layer may be very briefly heated to a substantially higher temperature (e.g., greater than 150° C., such as in the range of 300° C. to 700° C.) concomitantly with the application of one or more light pulses. In this manner, heat may be localized at a very superficial surface layer to kill surface microorganisms and inactivate surface enzymes, without significantly raising interior temperatures of the food product. For purposes of the invention, microorganisms are considered to be inactivated if they are either killed or rendered reproductively inactive. During the interval between successive pulses, the heat which is deposited in the surface layer of the foodstuff and/or packaging material may be conducted and dissipated without significantly altering the product. The number of light pulses and their total energy may be limited so as to maintain the measurable surface temperature of the material, ten seconds after pulsed light exposure, below about 100° C., and preferably to limit the surface temperature increase resulting from pulsed light treatment, at least 10 seconds after such treatment, to less than 50° C., and more preferably, less than 15° C.

In some embodiments, the foodstuff or other treated material may be substantially opaque to the light to which it is exposed so that very little light penetrates into the material and substantially all of the light (other than that which is reflected) is dissipated within a very superficial surface layer of the foodstuff, typically between less than about 1 micrometer and up to 1 millimeter thick. Light penetrates into a material surface according to an exponential formula:

$$I = (1-R) I_o e^{-ax} \quad (1)$$

where I is the energy intensity of the light transmitted to a distance x below the surface, R is the surface coefficient of reflection, $I_o$ is the intensity incident upon the surface, and a is extinction coefficient which measures the opacity to light of the material being used. The light which penetrates the material but is not transmitted is dissipated as heat in the material. At any point into the surface, the energy per unit are ($E_d$) dissipated in a depth, d, is given by the formula:

$$E_d = (1-R) I_o [1 - e^{-ad}] \quad (2)$$

As soon as the heat is deposited in the material through absorption of the light pulse, it begins to spread by thermal conduction generally in accordance with the well known law of heat transfer:

$$E_c = Akt \frac{dT}{dx} \quad (3)$$

where $E_c$ is the energy in the material which is conducted between two planes of area A separated by a unit of length dx, k is the thermal conductivity of the medium, dT is the difference of temperature between the two same planes in degrees Kelvin, and t is the time is seconds allowed for the heat conduction process to take place. In some embodiments, the treated material will have, or will be pretreated by means of an appropriate absorption enhancing agent to have an appropriate effective average absorption extinction coefficient over the desired spectral band of wavelengths to provide the desired absorption of energy within an appropriate depth.

When a beam of continuous light is absorbed at a food or packaging material surface, it is transformed into heat in the material generally according to equation (2); the heated surface becomes hotter, establishing a temperature gradient in the material and leading to a flow of heat into the deeper layers of the material at a rate set generally in accordance with equation (3). Eventually, a steady-state is established where the surface temperature is such that as much heat flows into the depth of the material as is deposited in the surface by the light beam. Because foods and other products often contain water, which is a good thermal conductor, heat produced at the product surface with conventional continuous light treatment processes (e.g., continuous mercury vapor ultraviolet light) may be quite rapidly conducted inward. However, by applying incoherent light pulses of high intensity and a duration which is short with respect to the thermal conductivity time constant, the energy may be deposited at the treated surface within a very short time, during which little or no thermal conduction takes place, substantially instantaneously heating a very thin surface layer to a temperature which is much higher than the steady-state temperature that is achieved by a continuous light beam of the same average power.

In accordance with certain aspects of the present invention, heating of a superficial layer of a relatively opaque food or packaging material is effected with light sources capable of producing pulses that each supply energy densities of between about 0.01 and about 50 joules per cm$^2$ and preferably between about 1 and 20 joules per cm$^2$ to the surface of the material during the duration of the pulse. For example, light pulses having an energy content between about 2 and about 20 joules per cm$^2$ (e.g., between about 8 and about 16 joules per cm$^2$) may readily and effectively be applied to the food surface. Typically, the energy density of the light pulses applied to the surface of the product is sufficient to produce pulsed thermal treatment of a very superficial surface layer. In order that the surface temperature is elevated before significant amounts are conducted interiorly, this energy is desirably supplied in pulses having a duration in the range of from about 0.001 to about 100 milliseconds, and preferably from about 0.1 to about 3 milliseconds, such as between about 0.1 and 1 millisecond. The duration of a pulse is determined by the elapsed time between when the rising light energy density of the light pulse is half of its peak value and when the intensity has fallen to half of its peak value. The total amount of light energy that will be supplied to each type of product depends upon properties of the particular material, such as its extinction (or absorption) coefficient and its surface coefficient of reflection. For methods utilizing surface heating, the requisite amount of heating for the particular product or packaging material also depends to a limited extent on the type or types of surface organisms, microbes, enzymes or viruses which must be destroyed. A wide variety of degradative organisms or enzymes may be present in food products, which may have a range of different optical absorption characteristics. By providing high intensity, broadband, polychromatic light pulses, food preservation against the effect of a broad range of microorganisms and degradative enzymes may be provided.

In this latter regard, many food products, particularly food products such as fruit, fish, shellfish, vegetables and meats, contain enzymes such as oxidoreductases, hydrolases, lipases, isomerases, proteinases, etc., which are capable of adversely affecting the appearance, odor, taste, stability or other palatability parameter of the food product upon storage. Degradative enzymes may, in particular, be present at cut or bruised surfaces of the food product. Enzymes may also be produced by microorganisms present on the surface of the food product. In accordance with various preferred aspects of treatment methods for such food products, the degradative activity of an enzyme may be reduced at least about 25% (i.e., less than 75% of the original activity is retained), and more preferably by a factor of at least about 90% (i.e., less than about 10% of the original emzyme activity is retained), over the food product surface. By food product surface is meant the exterior surface thickness of the food product to a depth of 0.1 millimeter. Although enzyme activity is characterized herein at the food product surface, enzyme inactivation may also be accomplished at food product zones internally of the food product surface. The broad spectrum, high intensity light pulses may be utilized to deactivate a wide variety of enzymes, thereby providing substantially simultaneous inactivation of a plurality of such enzymes. In this regard, in accordance with such methods, treatment with high intensity light pulses, as described herein, may be utilized to reduce the activity of each of a plurality of at least two different specific degradation food product enzymes by a factor of at least 25%, and preferably at least 90%, over the treated surface of the food product to provide a preserved food product having increased shelf life and stability. By simultaneously inactivating microorganisms and degradative enzymes by applying high intensity incoherent light pulses to food products in accordance with the present disclosure, synergistic preservation effects may be achieved.

For foodstuff treatment processes or other treatment processes in which it may be desired to limit the application of UV light to the product, the supplied light may be distributed primarily in wavelengths that range through the visible and into the far and near UV and near IR and preferably at least about 80% of the energy of the light pulse is distributed in the wavelength range between 270 and 2600 nanometers. For example, in certain specific treatment materials, the supplied light may be distributed primarily in wavelengths such that at least about 90% of the energy of the light is distributed in the wavelength between 300 and 2500 nanometers. Such light pulses may have at least about 10% of their light energy distributed in the near UV wavelengths, i.e., between 300 and 400 nanometers. However, visible and infrared light are also very effective in producing a dersired thermal surface effect. If desired, part or substantially all of the light at a predetermined cut-off frequency or a particular bandwidth may be eliminated, as by filtering, from the pulsed light spectrum. Such filtering may be accomplished by means of solid filters such as UV absorbing glass filters, or by liquid filters such as provided by a static or flowing liquid jacket surrounding a flashlamp having undesired spectral components. The liquid jacket may contain appropriate organic or inorganic absorption agents, such as inorganic salts which absorb at wavelengths which are to be removed. For example, a solution of copper sulfate in water used as a flashlamp cooling jacket medium (e.g., 50 grams $CuSO_4$ per gallon of water) provide an effective UV filter in the far UV. The absorption spectra of solid filter materials, liquids and solutions of organic and inorganic materials are well known, and may be selected as desired.

It is found that short, high intensity far and near UV pulses can very effectively deactivate vegetative and spore forms of microorganisms by thermal and/or photochemical means. Such pulses may also be effective in the inactivation of degradative food enzymes. The use of short, intense light pulses is found to allow a significant reduction in product processing time and significantly increase product throughput. However, pulsed visible and infrared light are also effective in producing the desired effect in highly absorptive media through surface heating. The ability to inactivate organisms, microbes, enzymes or viruses on surfaces with broad spectrum light makes it possible to more effectively inactivate degradative microorganisms (e.g., microbes, enzymes or viruses) by applying the incoherent, broad spectrum light pulses through transparent packaging materials, such as glass or clear plastic, some of which may tend to absorb certain ultraviolet wavelengths.

Much of the heat that is produced in the surface will eventually be conducted into the interior of the product; however, the total quantity of heat that is produced, even by a series of pulses, may be small relative to the amount of heat that would be needed to substantially raise the temperature in the interior of the product. Under these circumstances, the product (except for a very superficial surface layer) is not heated to a temperature that would substantially alter its characteristics. Moreover, the number of pulses used to reduce the microbiological burden on the surface of a product is desirably limited so as not to overheat the product.

A plurality of the closely spaced pulses of intense light, and in some cases a single pulse, will substantially reduce the population of microorganisms, typically by greater than about one order of magnitude (base 10) and preferably at least two orders of magnitude. Higher levels of reduction (including complete sterilization) may be accomplished at appropriate energy levels and treatment pulse numbers. Usually between about 1 and about 50 pulses of light are used to sufficiently treat a food, fluid, medical device or packaging material surface and preferably between about 1 and about 20 pulses are used. It is highly desirable that a plurality of at least 2 of the high intensity light pulses be applied.

In methods and apparatus directed to sterilization of food packaging materials, fluids such as air or water, or medical devices, (as well as some food processing methods) high energy light pulses which contain a substantial proportion of ultraviolet radiation may desirably be employed. If the surface that is being sterilized is of a food product container rather than a food product, the surface will commonly be subjected to between about 1 and about 20 pulses of light, typically from 1 to 3 pulses, to assure adequate microorganism inactivation. However, higher numbers of pulses, such as between 5 and 20 pulses, may be used with lower power levels, and/or to obtain increased deactivation.

The interval between pulses of high intensity light which are applied to a product and/or packaging material should be long enough for some of the heat to dissipate from the superficial surface layer, yet short enough so that the multiple pulses have cumulative effect. The time between pulses applied to the surface being treated desirably be generally between 0.001 seconds and about 30 seconds (e.g., 0.1 to 5 seconds), and preferably less than about 2 seconds in commercial processing or packaging applications. When the pulses are provided by a single flashlamp (or flashlamp assembly of a plurality of lamps which are flashed simultaneously), the maximum repetition rate is governed as a practical matter by individual lamp cooling parameters, which will typically provide a repetition rate in the range of from about less than 1 to about 1000 times per second. However, the effective repetition rate may be increased by employing multiple flashlamps which are sequentially flashed, and by providing relative movement between the flashlamp and the surface being treated.

Incoherent pulsed light of sufficient intensity as well as appropriate duration and wavelength distribution is obtainable from a flashlamp system. A suitable flashlamp system is sold by Maxwell Laboratories, Inc., under the trademark Flashblast. A particular model, the Flashblast Model FB-300, consists of a DC power supply which charges energy storage capacitors, a switch used to control the discharge of these capacitors, a trigger circuit to fire the switch at pre-programmed time intervals (automatic mode) or when a button is depressed by the operator (manual mode), a set of high voltage coaxial cables carrying the discharge pulses from the capacitor-switch assembly, and from one to four flashlamps mounted in metal reflectors to direct the light emitted from the lamps.

In order to enhance the effect of high intensity, pulsed incoherent light treatment, particularly for transparent, reflective or relatively nonabsorbent food products or substrates, a suitable absorption enhancing agent may be applied to the surface of the packaging substrate or food product. Two principal applications of this technique involve surface treatment of products which may be relatively transparent to the wavelengths of light chosen for treatment. For example some foods, such as certain fruits, juices or thin filets of fresh fish, are relatively transparent to visible light.

In accordance with various aspects of such methods, an absorption enhancing agent may first be applied to the product surface to be treated. The agent may be applied in any suitable manner, such as by spraying or dusting the surface of the product with a powder containing the agent or by applying the agent as a dissolved liquid, such as aqueous or nonaqueous solution of the agent which may be applied by spraying, coating or immersing the substrate to be treated, or by vaporizing the agent onto the surface of the packaging material or the product.

Suitable absorption enhancing agents should have a high optical absorption coefficient at the spectral wavelengths desired, within the spectral range of the high intensity light pulse(s) used in the treatment. Although the agent may be substantially completely removed from the product by the processing, for food products and medical devices, the agent should best be an edible material which is generally recognized as safe and which may be readily applied to food products, devices or packaging surfaces which are to contact the surface of the food product.

Desirably, the agent may be selectively absorbed onto living cell surfaces, so that the amount of agent used may be minimized or its effect concentrated. Indicator agents such as dyes which are photon sensitive, pH sensitive or which are sensitive to oxidation potential may be utilized to processing advantage, so that the photonic absorption of the agent may be varied as part of the treatment process. Such indicator dyes may be useful for particular food products, packaging films or treatment procedures in which the dye absorption is increased or decreased during pulsed light treatment. Absorption enhancing agents may desirably be selected which vaporize without decomposition or which have benign decomposition products. Examples of agents include approved Food, Drug and Cosmetic colors such as carotene, red dye #3, lime green, black cherry and mixtures thereof. The various natural dyes and natural food colorings may desirably be used for food product processing as may various natural or cooking oils. Mixtures of two or more components having different absorption maxima may desirably be used to increase optical absorption over the desired spectrum. Absorption agents which have an affinity for bacteria or enzymes may also be selected to enhance preservation treatment of food products.

After application of the absorption enhancing agent to the product surface from solution (such as by dipping, spraying or roll coating), excess solution may be removed, and the surface of the product may be partially or completely dried if desired. The product may subsequently be subjected to pulsed incoherent light treatment, to heat a very thin surface layer, which has been subjected to agent treatment, in a time which is small compared to the time required for thermal conduction.

The use of absorption enhancing agents for pretreatment of products may allow the pulse width of the light provided by the flash apparatus to be increased. This has the effect of lowering the ultraviolet content, shifting the output of the flashlamps to longer wavelengths and increasing the service life of the flashlamps.

In methods which employ the pulsed light treatment of product surfaces, the product is desirably treated over its entire surface. This may be accomplished by treatment of the product through a transparent conveyor (or conveyor having transparent sections on which the product is placed), by turning the product during a multiple exposure treatment involving a series of light pulses, or by a free fall treatment in which the product falls through a treatment zone surrounded by flashlamps so that substantially the entire surface of the food product is subjected to simultaneous treatment. Passage of the product through a trigger sensor zone may be utilized to time the flashlamp pulses with the presence of the product, with multiple banks of flashlamps being timed to free fall conditions of the product. A sterilized air flow may desirably be used, in a direction countercurrent to the product flow. Sterilized air may be provided in a conventional manner, but also may desirably be provided by continuously conducting air through a high intensity pulsed light treatment zone and subjecting all of the air to a plurality of preferably UV enriched high intensity polychromatic light pulses, at the intensity levels and durations previously described, as it passes through the zone. For some products, such as fresh fish, a preliminary high pressure water wash may be desirable. In order to remove surface-heated products or a surface "cooked" flavor which may be present on the food product, a final wash with sterile water or other agents may also be used if appropriate. The product may also be enclosed in a transparent wrapping material prior to pulsed light treatment.

Having generally described the present invention, various aspects of the invention will now be more fully described with respect to the specific embodiments illustrated in the FIGURES and various Examples. In this regard, illustrated in FIG. 1, is an aseptic packaging apparatus 10 in which a reel of conventional flexible aseptic packaging material 102 is optionally directed by means of a series of rollers 104 in accordance with conventional practice, to a solution of an optional absorption enhancing agent as previously described, in dipping-trough 106. The packaging material may typically comprise a layered structure of one or more internal coating and sealing layers, a metal foil such as aluminum foil, a laminating layer or paper layer and an external layer, in accordance with conventional practice.

Excess absorption enhancing agent solution may be removed by rollers 110, with the film being subsequently formed into a longitudinally sealed tube by longitudinal sealing apparatus 112. Depending upon whether a lap seal or a fin seal is desired, a strip 108 may be applied to one edge of the packaging material to reinforce the longitudinal seam, and to prevent the product from coming into contact with the edge of the film 102.

An important aspect of aseptic packaging apparatus 10 is product filling and flashlamp assembly 200 which is shown in more detail in FIG. 2. The illustrated assembly 200 comprises an outer support tube 202, having attached thereto one or more flashlamps 204 distributed about and along the tube 202 such that upon pulsing, the entire inner surface of the sealed packaging material tube is subject to intense, short duration incoherent light pulses. A variety of arrangements of the flashlamps along the support tube 202 is feasible, the essential feature being that the entire inner surface of the packaging material tube is exposed to the pulsed light. Internally of the support tube 202 is a sterile food product tube 206, and flashlamp electrical cable 208 and optional lamp coolant lines 210 may be located intermediate the tubes 202, 206. In addition, sterile air provided under pressure from a suitable supply (not shown) may be conducted for discharge within the sealed tube. Sterile air may be produced by a variety of techniques (filtration, incineration) including the use of intense incoherent light pulses as described herein. In operation, the longitudinally sealed film tube, which is transversely sealed by a suitable transverse sealing apparatus 114 has introduced therein a predetermined portion of substantially sterile food product 212. The sterilized food product may be produced by short time, high temperature processing or by other processes. The longitudinally sealed film tube is advanced one package length, while the flashlamp assembly is pulsed a plurality of times in order to repeatedly sterilize the entire adjacent interior of the tube above the food product 212. Sterile air 220 exits the support tube 202 and is carried over the flashlamp assemblies to cool the flashlamps and to remove from the longitudinally sealed film tube any ablation products produced by the flashlamp discharge and to prevent contamination from settling on the treated area. Following transverse sealing, the packages may be separated into individual consumer packages 116.

The present method may also be applied to other types of aseptic packaging systems, such as those which utilize preformed product containers. In this regard, illustrated in FIG. 3 is aseptic packaging apparatus 30. The packaging apparatus 30 utilizes preformed product containers 302 which are introduced into the sterilization zone 304 of the apparatus 30. Optionally an absorption enhancing agent solution as previously described may be sprayed into containers 302 by means of spraying apparatus 306. Subsequently, the containers progressively pass through a plurality of flashlamp treatment stations 308 in which reciprocating "U" shaped flashlamps, linear flashlamps, bulb type flashlamps and/or flashlamps of other configurations are introduced above or into the container openings and the flashlamps pulsed at least once per container 302. The treatment stations are then withdrawn and the containers are advanced by one station, as the process is repeated so that the entire interior surface of each of the containers is subjected to a plurality of intense incoherent light pulses as it progresses along the treatment stations. A sterile air purge apparatus may also be utilized to remove any material ablated from the interior of the containers and to prevent contamination from settling in the treated containers and to cool the flashlamps. A suitable stationary battery of flashlamps may also be provided to treat the exterior and edge surfaces of the containers upon their passage through the flashlamp treatment zone if desired. The sterilized containers subsequently pass through the filling station 312 where a preprocessed food product is introduced into the container, which is subsequently sealed at the top by a sterile lid.

A laminar, sterile air curtain may be provided over the entire aseptic packaging apparatus 30 in order to prevent the infection of the packaged units. The sterile air may be provided by gas sterilization apparatus 350 which includes an air input blower 352, which pumps air through filter 354 to a pulsed light treatment zone 356 containing a bank of high power Xenon flashlamps 358 enclosed in a reflective housing 360. The air is continuously forced through the zone 356 at a rate which inconjunction with the pulse rate of the lamps 358, insures that all of the air is subjected to a plurality of high intensity polychromatic incoherent light pulses as previously described, as it passes through the zone 356. Desirably, the light pulses will be a UV rich (e.g., having at least 5 percent of the light energy at wavelengths shorter than 300 nanometers) and will desirably have an energy density of at least 0.5 joule per square centimeter throughout the treatment zone through which all of the air passes. The pulse duration may typically be in the range of from about 0.1 to 3 milliseconds. The multiple-lamp reflector array provides multidirectional, substantially even illumination to the air or other gas flowing therethrough, so that a dust particle or bacterial colony forming unit is treated from all sides and is not self-shielded. This multidirectional treatment is an important feature of the system 350. Other arrangements for fluid treatment, such as shown in FIGS. 5 and 6, may be utilized for the air treatment system 350.

Illustrated in FIG. 4 is an additional embodiment of an aseptic packaging apparatus 40 which comprises two reels 402, 404 of plastic packaging material, one for the body of the finished packages and one for package lids. The container body material may be conducted through an optional absorption enhancing agent bath 406 as previously described. The packaging material 402 may be conducted through a suction and drier section to remove excess agent solution. The packaging material is subsequently subjected to intense incoherent light pulses by an array 408 of flashlamps extended longitudinally along the direction of travel of the packaging material, following which the packaging material 402 may be thermoformed into suitable containers and forming apparatus 410 which are then filled with an aseptically processed foodstuff at filling station 412. The lid material may similarly optionally be passed through an absorption enhancing agent bath 414, subjected to a plurality of intense incoherent light pulses by flashlamp array 416 and utilized to seal the filled, formed containers. The entire apparatus may be maintained under sterile air blanket.

FIG. 5a is a schematic view of an embodiment for the treatment of pumpable products such as water or liquid food products such as fruit juices with intense incoherent pulsed light. The apparatus 50 comprises a reflective, cylindrical enclosure defining a treatment chamber 502 through which the product flows and which surrounds a pulsed light source 504, which in the embodiment 50 is a high intensity Xenon flashlamp provided with a suitable power source (not shown) in accordance with conventional practice for flashlamp operation. A liquid circulation pump 508 controls the flow rate of the product through the treatment chamber 502 in respect to the pulse repetition rate of the pulsed light sources so that during the product residence time within the treatment chamber 502, all of the product which passes therethrough receives a predetermined number of high intensity pulses of incoherent, polychromatic light. The product exiting the treatment chamber 502 will therefore be sterile or disinfected to the degree desired. In some embodiments, the product treatment chamber 502 will be suitably arranged so as to be separated from the pulsed light source 504 so as to prevent the product from contacting the source. The diameter of the treatment chamber will vary depending upon many factors including but not limited to the specific absorption characteristics of the product to be treated, the physical and operating characteristics of the flashlamps and the degree of product mixing between multiple pulses. The treatment chamber may be suitably designed to include a reflector assembly as its outer wall or as an external reflector, in order to reflect illumination traversing the product back inward. It is noted that fluids such as air and water are relatively transparent to light, including significant portions of the UV spectrum. Accordingly, there is relatively little attenuation, through absorption in such media, with the flux density decreasing largely only as a function of distance from the control lamp. However, for fluids which have significant absorption, this factor will also decrease the pulse flux intensity as a function of distance from the lamp. In any event, the desired minimum flux density, as previously described, should be maintained throughout the treatment zone or mixing must occur to insure that all of the fluid is subjected to the appropriate flux intensity and number of pulses.

While the lamp is located internally of the treatment chamber 502 in the apparatus 50, one or more lamps may also be located externally of the treatment chamber. A particularly preferred design is shown in FIG. 5b in which the liquid to be treated is conducted through a transparent treatment conduit (e.g., a quartz glass tube) 552 which is positioned along one focus of an elliptical reflector 554. A flashlamp 556 is positioned along another focus of the elliptical reflector with multiple elliptical segments each having a lamp at one focus and the quartz tube 552 at the other focus (not shown) being utilized if desired. The lamp may be jacketed for water cooling and/or liquid spectral filtering. In this manner, because the light pulses are focused toward the center of the liquid treatment zone, compensation is provided for the light absorption of the liquid being treated, so that all of the liquid is subjected to more uniform light treatment.

Illustrated in FIG. 6 is an embodiment of an intense incoherent light processing station 60 comprising a pulsed light source/reflector array 602 through which the product 601 passes, falls or tumbles. The flashlamp reflector array 602 is connected by umbilicals to an electrical pulse forming network 603 or pulser which energizes the flashlamp array either simultaneously or sequentially and a cooling/filtering liquid circulator 604 which circulates liquid medium through a jacket assembly external to each lamp for cooling and/or spectral filtering by the use of selected solutions with the desired spectral transmittance/absorbance characteristics. The flashlamp/reflector array comprises a plurality of lamps and reflectors which create an intense light pulse treatment region. While the illustrated embodiment 60 uses straight lamps and reflector elements, other arrangements may be utilized. For example, flashlamps may be constructed in any shape in much the same way that neon lighting signs may also be made to any shape. Similarly, reflectors may be made of many different materials in many different geometries to accommodate imaging the flashlamp source upon the treated product in the desired mode. "The Optical Design of Reflectors", Second Edition, William B. Elmer, Published by John Wiley and Sons, Inc., N.Y. is an appropriate resource as an introduction to the fundamentals of reflector design.

Although the present invention includes many potential applications for the reduction of viable organisms, microbe or virus numbers or enzymatic activity in the preservation of food products, the use of high intensity, short time duration light treatment for the sterilization of packaging materials in aseptic packaging methods is considered an important aspect of the present disclosure. In such packaging methods, generally the full broad spectrum flashlamp output including near and far ultraviolet light components of the spectrum will normally be employed, so that relatively low fluences may be utilized. For example, even at very high organism densities (up to $1 \times 10^6$ to $1 \times 10^8$ CFU/cm$^2$), only one or two flashes at an energy density of 1.5 J/cm2 per flash will result in sterilization of spores and vegetative bacteria and viruses.

When, as is preferred, the flashlamp spectra includes at least about 10 percent of its energy at wavelengths shorter than about 300 nanometers or when the product itself is sufficiently absorptive to provide the desired spectral interaction, the absorption enhancing agent bath of the aseptic packaging apparatus, as previously described may desirably be elminated. For high speed operation and high power densities, it may be desirable to cool the flashlamps by optional water jacket. For transparent wrapping or other packaging materials, it may also be desirable to provide a lamp array externally of the longitudinally sealed film, so that only the product and countercurrent sterile air tube is inserted in the film tube.

Having generally described the present invention, various aspects of the invention will now be described in greater detail by way of the following sepcific examples. These examples demonstrate qualitatively and quantitatively the effectiveness of the invention for preserving food products by reducing or eliminating microorganisms and enzymes. In some examples, microorganisms were deliberately introduced onto the surfaces of food products or packaging materials to be treated and in other examples the food products were treated to remove the naturally occurring degradative enzymes and/or microorganisms. It is noted that the deliberate application of very high densities of microorganisms to foodstuff or other surfaces produces a high degree of self-shielding of the microorganisms. This high degree of self-shielding increases the intensity and/or number of pulses of light required to achieve a given ratio of reduction of colony forming units over that required for the same reduction ratio for a lower density of indigenous colony forming units. Accordingly, these examples using high microorganism density represent a dramatic demonstration of the effectiveness of the pulsed light treatment.

EXAMPLE 1

Curds of a commercially-sold, dry (non-creamed) cottage cheese are carefully separated and submerged in a liquid culture of Pseudomonas bacteria. Excess culture liquid is drained from the curds, and the curds are divided in several portions and spread in monolayers onto sterilized stainless steel sheets. The sheets were placed in a refrigerator and maintained at 38° F. for one hour. The sheets are removed from the refrigerator, one at a time, for treatment using a flashlamp system (Flashblast Model FB-100 pulsed light system of Maxwell Laboratories, Inc.) which produced pulses of about 0.5 millisecond duration, providing 16 J/cm$^2$ energy density per pulse directed at the curds in 3 second intervals.

Immediately following exposure to the light pulses, the temperature of five curds is measured with thermal probes at the surfaces of the curds closest to the light source. From the corresponding surfaces of three other curds, 1 cm$^2$ plugs are taken and the plugs are individually transferred to 1 ml. aliquots of sterilized solution and mixed vigorously to form slurries. The slurries are individually plated on a standard bacteriological medium and a cell count of each is taken. The three cell counts from each sample are averaged.

The number of pulses to which the curds on each sheet are exposed are as follows, 0, 1 and 2 . As a control, the curds on one sheet are not exposed to the light pulses and plugs are taken from three of these curds to determine the cell count of an unprocessed curd.

The results are listed in the table below. Percentage of viability reduction (PVR) was calculated by the formula [(1-cell counts exposed sample/cell counts control)$\times$100].

| Pulses | Average Cell Counts | PVR % | Temp (°F.) |
|---|---|---|---|
| 0 (control) | 4500 | 0 | 40 |
| 1 | 950 | 78.9 | 42 |
| 2 | 150 | 96.7 | 43 |

There is no visible discoloration of any of the curds exposed to flashlamp light.

EXAMPLE 2

Curds of cottage cheese are spread on trays as was done in Example 1 except that this time the curds are not submerged in culture. Half of the trays are subjected to 2 pulses of flashlamp illumination under the conditions of Example 1 and half are not treated. The treated curds and the untreated curds are then gathered up.

A panel of experienced taste testers is asked to râte taste characteristics of blindly administered samples of the treated and untreated samples. Thus, under surface sterilization condition which produce a PVR of 96.7% (see Example 1), the taste of a dairy product is substantially unaffected.

EXAMPLE 3

Hard crusted white bread rolls are tumbled in a stream of air which was passed over a common bread mold, for the purpose of entraining mold spores and contaminating the surface of the rolls. Individual rolls are placed on stainless steel trays and are subjected to high intensity incoherent light pulses produced by a flashlamp system. Set on automatic mode, the system produces pulses of about 0.5 millisecond duration delivering 16 J/cm$^2$ of light to the bread roll surfaces every 5 seconds. Rolls are exposed to the following number of pulses: 0, 1 and 2. Immediately after exposure, the surface temperature of the rolls is measured.

With sterilized blade, a 10 cm$^2$ section of crust is cut from the surface of each roll closest to the light source. The crust is slurried, plated on bacteriological medium, and counts are taken after appropriate incubation.

The results are as follows:

| Pulses | Average Cell Counts | PVR % | Temp (°F.) |
|---|---|---|---|
| 0 (control) | 3000 | 0 | 95 |
| 1 | 85 | 97.2 | 95 |
| 2 | 6 | 99.8 | 106 |

No charring of any of the rolls is observed, demonstrating that methods in accordance with the present invention may be utilized to thermally inactivate microorganisms without burning the food product.

EXAMPLE 4

Squares of a freshly baked cake are subjected to a flow of air entraining mold spores. Then the cake squares are placed in rectangularly shaped, open-top packaging containers formed of clear plastic and sealed with a clear plastic top. Half of the cake squares are treated while sealed within the plastic and half of the cake squares are not treated.

The squares are treated with the FB-300 system. The system exposes the cake to 3 pulses at 5 second intervals delivering 16 J/cm$^2$ per pulse to the surface of the cake. Each cake is then turned to expose a different surface and the process is repeated until all six sides of the cake square are processed. No effects of the treatment are visible on any of the six sides.

The samples are stored at room temperature in their sealed packages and are observed daily for visible appearance of molds. All of the untreated cake squares exhibit visible mold growth within 3 days. None of the treated pieces exhibit mold spores before 8 days have passed. The average number of days before visible mold growth appears on the treated squares is 10.

EXAMPLE 5

Microorganisms are important agents of deterioration in fresh fish because they are responsible for undesirable odors and flavors associated with spoilage. Consequently, the problem of control of deterioration of fresh fish is largely a problem of control of the microorganisms associated with spoilage.

A series of tests were carried out in which summer flounder was treated with light pulses by means of the FB-300 flashlamp apparatus of Maxwell Laboratories, Inc. The various retail market forms of the flounder were whole, scaled, unscaled and filets from the viscera and skin sides. A high pressure wash treatment employing a water spray at 650 psi was also used for a number of the samples. It is noted that the darker fish sample absorbed substantially more energy per exposure than the lighter sample. The results of these tests are set forth in the following table:

TABLE 1

The Effect of One and Three 10 Joule per Square Centimeter Xenon Flashlamp Exposures on the Coliform and Psychrotrophic Organisms on the Dark Side of Summer Flounder

| Sample Description | Flashblast Exposures* | Coliforms | Psychrotrophs |
|---|---|---|---|
| Whole unscaled | 0**** | $2.8 \times 10^{5}$** | $5.0 \times 10^{6}$ |
|  | 1 | $1.2 \times 10^{5}$** | $6.5 \times 10^{5}$ |
|  | 3 | $8.4 \times 10^{3}$ | $4.3 \times 10^{4}$ |
| Whole scaled | 0**** | $2.8 \times 10^{5}$** | $1.9 \times 10^{6}$ |
|  | 1 | $4.9 \times 10^{4}$** | $2.0 \times 10^{5}$ |
|  | 3 | $3.3 \times 10^{3}$ | $1.9 \times 10^{4}$ |
| Filet (viscera side) | 0**** | $1.9 \times 10^{4}$ | $1.1 \times 10^{5}$ |
|  | 1 | $5.3 \times 10^{3}$ | $2.1 \times 10^{4}$ |
|  | 3 | $5.0 \times 10^{3}$ | $1.4 \times 10^{4}$ |
| Filet (skin side skin removed) | 0**** | $1.2 \times 10^{0}$ | —*** |
|  | 1 | $1.4 \times 10^{2}$ | $4.0 \times 10^{2}$** |
|  | 3 | $5.0 \times 10^{0}$** | $5.0 \times 10^{1}$** |
| Whole scaled High pressure wash | 0**** | $1.4 \times 10^{3}$ | $5.3 \times 10^{3}$ |
|  | 1 | $8.8 \times 10^{1}$ | $1.5 \times 10^{2}$** |
|  | 3 | $9.0 \times 10^{1}$ | $8.0 \times 10^{2}$ |

*10 Joules per pulse (34 microamperes)
**estimated, count was above or below dilution
***0 exposure is the control treatment
****sample discarded from study

TABLE 1A

The Effect of One and Three 10 Joule per Square Centimeter Xenon Flashlamp Exposures on the Coliform and Psychrotrophic Organisms on the White Side of Summer Flounder

| Sample Description | Flashblast Exposures* | Coliforms | Psychrotrophs |
|---|---|---|---|
| Whole unscaled | 0**** | $1.4 \times 10^{4}$ | $3.8 \times 10^{5}$ |
|  | 1 | $8.9 \times 10^{3}$ | $7.3 \times 10^{4}$ |
|  | 3 | $1.6 \times 10^{2}$ | $5.5 \times 10^{3}$ |
| Whole scaled | 0**** | $9.3 \times 10^{4}$** | $3.1 \times 10^{5}$ |
|  | 1 | $2.9 \times 10^{3}$ | $3.0 \times 10^{4}$ |
|  | 3 | $1.0 \times 10^{3}$ | $7.8 \times 10^{3}$ |
| Filet (viscera side) | 0**** | $7.4 \times 10^{4}$** | $1.1 \times 10^{5}$ |
|  | 1 | $1.7 \times 10^{3}$ | $3.0 \times 10^{3}$ |
|  | 3 | $3.7 \times 10^{2}$ | $6.8 \times 10^{2}$ |
| Filet (skin side skin removed) | 0**** | $6.5 \times 10^{2}$ | $2.0 \times 10^{3}$ |
|  | 1 | $3.3 \times 10^{2}$ | $7.8 \times 10^{2}$ |
|  | 3 | $3.5 \times 10^{1}$** | $5.0 \times 10^{1}$** |

*10 Joules per pulse
**estimated, count was above or below dilution
***0 exposure is the control treatment
****sample discarded from study When the pulsed incoherent light treatment was used in combination with the high pressure wash treatment (Tables 1 and 1A), both the psychrotroph and coliform burden on the fish samples were reduced. The reduction achieved is significant in terms of product quality and marketing considerations of increased shelf life, reduced product loss and expansion of marketing area for fresh fish.

The temperature near the surface of the flounder was measured before and after three 10 Joule/cm² light pulses near the surface. An average rise of 16° F. (66° F. to 82° F.) was obtained. It is noted that the temperature increase is a bulk temperature increase measured after a time which is long with respect to thermal conduction times, and does not correspond to the much higher temperature increase of a very thin surface layer contemporaneously with the pulsed light treatment. It is desirable to cool the fish before and after pulsed light treatment to refrigeration temperature in the range of from about 32° to about 45° F. in commercial practice to compensate for this temperature increase, which is favorable to microorganism growth and product autolysis.

A further series of tests were carried out to determine the effects of pulsed incoherent light intensity and number of exposures on fish surface microorganisms. The pulsed light intensities employed to the fish surface undergoing treatment was nominally selected to be 2, 5 and 10 Joules/cm² and the number of exposures at each treatment was 1, 3 and 5, respectively. The intensity of the pulsed light was varied by varying the distance of the sample to the flashlamps, which were used without the water jacket. Fresh flounder filets, both dark and white sides, were used in the study, with only the scaled skin surface being used to prevent sample variation. Result of the study are set forth in Table 3.

TABLE 3

The Effect of Pulsed Light Intensity and Number of Exposures on Reducing the Psychrotrophs of Fresh Flounder Filets

| Sample Description | Flashblast Intensity (Joules) | Flashblast Exposures (Number) | Colony Forming Units in Surface Area (Psychrotrophs) |
|---|---|---|---|
| Filet, flesh side | 2 | 0 | $2.5 \times 10^{4}$ |
|  | 2 | 1 | $3.0 \times 10^{4}$ |
|  | 2 | 3 | $1.6 \times 10^{4}$ |
|  | 2 | 5 | $2.1 \times 10^{4}$ |
|  | 5 | 0 | $2.5 \times 10^{5}$ |
|  | 5 | 1 | $4.5 \times 10^{4}$ |
|  | 5 | 3 | $6.4 \times 10^{4}$ |
|  | 5 | 5 | $5.8 \times 10^{4}$ |
|  | 10 | 0 | $1.6 \times 10^{5}$ |
|  | 10 | 1 | $1.9 \times 10^{4}$ |
|  | 10 | 3 | $4.2 \times 10^{3}$ |

The largest reduction in counts occurred in those samples receiving 10 Joule/cm² treatments. Little, if any, reduction in counts occurred when a 2 Joule intensity was used irrespective of the exposure number.

A high pressure water wash is known to be effective in removing the surface contamination of seafood products. Such a high pressure water was tested alone and in combination with pulsed light exposure as previously described in respect to the tests of Tables 2 and 3. The treated fish samples were subjected to tray pack storage at 33° F. A sensory panel was conducted concomitantly with the refrigerated microbial storage stability study to determine how the organoleptic properties of the products was effected. The following Table 4 contains the microbiological information during 15 days of tray pack storage at 33° F.

TABLE 4

Microbiological Counts of Fresh and High Pressure Wash Flounder Filets With and Without Pulsed Light Treatment stored at 33° F.

| Storage Day & Type | Fresh | Fresh w/ Pulsed Light Treatment | High Pressure Wash | High Pressure Wash w/Pulsed Light Treat |
|---|---|---|---|---|
| 1-C | $3.5 \times 10^{1}$ | $1.0 \times 10^{1}$ | $1.0 \times 10^{1}$** | $1.0 \times 10^{1}$** |
| 1-P | $2.4 \times 10^{1}$ | $6.5 \times 10^{1}$ | $6.7 \times 10^{2}$ | $6.3 \times 10^{2}$ |
| 6-C | $7.6 \times 10^{1}$ | $1.2 \times 10^{2}$ | $1.0 \times 10^{1}$** | $1.0 \times 10^{1}$** |
| 6-P | $6.9 \times 10^{5}$ | $3.0 \times 10^{5}$ | $5.5 \times 10^{4}$ | $2.7 \times 10^{3}$ |

TABLE 4-continued

Microbiological Counts of Fresh and High Pressure Wash Flounder Filets With and Without Pulsed Light Treatment stored at 33° F.

| Storage Day & Type | Fresh | Fresh w/ Pulsed Light Treatment | High Pressure Wash | High Pressure Wash w/Pulsed Light Treat |
|---|---|---|---|---|
| 10-C | $2.3 \times 10^3$ | $3.2 \times 10^2$ | $1.0 \times 10^{1**}$ | $1.0 \times 10^{1**}$ |
| 10-P | $2.5 \times 10^8$ | $2.9 \times 10^7$ | $8.9 \times 10^6$ | $8.5 \times 10^5$ |
| 13-C | $2.4 \times 10^4$ | $3.8 \times 10^3$ | $3.0 \times 10^2$ | $1.0 \times 10^{1**}$ |
| 13-P | $7.8 \times 10^8$ | $3.0 \times 10^8$ | $4.2 \times 10^7$ | $1.5 \times 10^7$ |
| 15-C | $2.9 \times 10^4$ | $7.0 \times 10^3$ | $8.3 \times 10^1$ | $1.4 \times 10^2$ |
| 15-P | $1.9 \times 10^9$ | $4.0 \times 10^8$ | $1.9_{10}8$ | $6.0 \times 10^7$ |

Organism Type - C = coliforms;
P = psychrotrophs
*pulsed light treatment was 2 exposures at 5 Joules on both sides of filet
**estimated, count was above or below dilution The combination of high pressure wash and pulsed light treatment was the most effective treatment with reductions approaching three logs (99.9%).

Sensory analysis data is presented in Table 5 and 5A.

TABLE 5

Sensory Scores of Fresh Flounder Filets Treated with Pulsed Light Treatment and Stored at 33° F.

| Storage Day | Fresh | | | | | Fresh w/Pulsed Light Tr | | | | |
|---|---|---|---|---|---|---|---|---|---|---|
|  | O | A | t | T | Avg | O | A | t | T | Avg |
| 1  | 5.1 | 6.0 | 6.3 | 6.3 | 6.0 | 3.1 | 4.3 | 4.1 | 4.4 | 4.0 |
| 6  | 5.0 | 5.6 | 5.1 | 5.0 | 5.1 | 3.0 | 5.0 | 3.3 | 3.6 | 3.7 |
| 10 | 3.1 | 4.7 | 3.1 | 3.9 | 3.7 | 3.8 | 4.4 | 3.2 | 3.3 | 3.7 |
| 13 | 3.1 | 4.0 | 2.4 | 3.1 | 3.2 | 2.8 | 3.8 | 2.9 | 3.9 | 3.4 |
| 15 | 1.2 | 2.3 | 0.7 | 1.2 | 1.4 | 2.3 | 2.5 | 2.2 | 2.7 | 2.4 |

O = odor;
A = appearance;
t = taste;
T = texture
0 - refused;
1 - dislike extremely;
2 - dislike moderately;
3 - dislike slightly;
4 - neither like nor dislike;
5 - like slightly;
6 - like moderately;
7 - like extremely

TABLE 5A

Sensory Scores of High Pressure Wash and Fresh Flounder Filets with Pulsed Light Treatment and Stored at 33° F.

| Storage Day | Fresh | | | | | Fresh w/Pulsed Light Trt | | | | |
|---|---|---|---|---|---|---|---|---|---|---|
|  | O | A | t | T | Avg | O | A | t | T | Avg |
| 1  | 4.9 | 5.6 | 5.5 | 5.1 | 5.3 | 3.9 | 5.4 | 4.3 | 5.1 | 4.7 |
| 6  | 5.1 | 5.6 | 5.8 | 5.4 | 5.5 | 3.4 | 4.8 | 4.6 | 4.6 | 4.4 |
| 10 | 3.6 | 4.8 | 3.4 | 3.9 | 3.9 | 3.3 | 4.2 | 2.7 | 3.1 | 3.3 |
| 13 | 3.9 | 3.8 | 3.3 | 3.9 | 3.7 | 4.1 | 4.6 | 4.1 | 4.5 | 4.3 |
| 15 | 3.0 | 3.7 | 2.8 | 2.8 | 3.0 | 4.3 | 4.8 | 4.0 | 4.1 | 4.3 |

O = odor;
A = appearance;
t = taste;
T = texture
0 - refused;
1 - dislike extremely;
2 - dislike moderately;
3 - dislike slightly;
4 - neither like nor dislike;
5 - like slightly;
6 - like moderately;
7 - like extremely The combination pulsed light and high pressure washed fish samples were acceptable past the 15th day of storage, with a projected acceptability of until the 17th or 19th day.

These tests demonstrate that intense incoherent pulsed light treatment is effective in lowering the surface coliform and psychrotroph populations on food products such as fresh fish. This reduction is capable of extending product shelf-life and therefore not only reduces product loss but also enables the development of improved marketing and distribution of fresh fish.

Other natural meat products such as beef, poultry (e.g., chicken, turkey) and pork, particularly in sliced form, and prepared or processed meat products such as sausages and ground meat patties, may readily be treated to provide food products having increased shelf life, under refrigeration without the necessity for freezing. Because vegetables, fruits and prepared food products such as pastas and rice entrees may be similarly treated, prepared meals including meat and other entrees may be surface treated with pulsed incoherent light and packaged to provide individual prepared meals having increased storage stability under refrigeration and without the necessity for subjecting the packaged products to the costs and effects of freezing.

EXAMPLE 6

In order to demonstrate the effectiveness of intense, pulsed incoherent light flashes in aseptic packaging and food preservation uses, a series of tests were carried out in which cultures of various microorganisms, which are representative of naturally occurring food spoilage microorganisms, were inoculated onto the surface of a culture medium. The inoculated culture medium subsequently was subjected to intense, incoherent pulsed light under a variety of test conditions. The light pulses were provided by the FB-300 Flashblast pulsed light generation system of Maxwell Laboratories, Inc. The FB-300 Flashblast pulsed light system has a linear Xenon flashlamp in a reflective housing through which is discharged, under control of a high current switch, a 745 microfared capacitor bank which may be charged to 2600 volts to produce a maximum energy of 2500 Joules. The Xenon flashlamp has a highly UV transmissive fused quartz envelope with a 7 millimeter bore, an arc length of about 9 inches and was filled with Xenon at a pressure of 450 Torr.

The spatial photolamp reflector housing of the pulsed light system used in the following examples was designed for no more than a 25% fluence variation over a sample test area of one inch by four inches.

Stock *Aspegillus niger* and *Saccharomyces cerevisiae* cultures were grown on Potato Dextrose Agar (PDA) (pH 5.6, not further acidified with tartaric acid) at 25° C. *Aspergillus niger* mold spore suspensions were collected in 0.1% sterile Tergitol 7 (anionic) and treatment platings carried out on PDA containing 0.05% Rose Bengal (acid red 94: tetraiodotetracholorofluorescein, Na Salt) to inihibit mycelial spreading. *Saccharomyces cerevisiae* and all other microbial cultures except *Aspergillus niger* were treated on Tryptic Soy Agar (DIFCO). *Bacillus subtilis* vegetative cultures were grown in 15 ml of Tryptic Soy Broth as an unshaken flat culture in a 10×100 mm petri at 35° C. Other bacterial cultures were grown as 10 ml deep at 35° C. The *Bacillus subtilis* spore suspension was a purified spore population containing greater than 95% spores and was stored in distilled water at 4° C. and diluted for plating immediately prior to treatment. Fungal cultures were incubated at 25° C. while bacterial cultures were incubated at 35° C.

Stock cultures, the *Bacillus subtilis* spore suspension and *Aspergillus niger* spore suspension were diluted serially prior to treatment in sterile 1/10th strength tryptic soy broth. Twenty-five microliter droplets of the undiluted stock suspension and $1 \times 10^{-1}$ through $1 \times 10^{-6}$ dilutions of the stock suspension were spotted in two rows along the central chord of a petri dish containing approximately 15 ml of tryptic soy agar. The approximate width of the two row spot pattern was slightly less than 2.5 cm (one inch). The droplets were air dried at 35° C. and then exposed to intense, incoherent pulsed light.

After exposure and incubation of plates, the growth patterns of control and exposed plates were examined. The growth pattern on treated plates was recorded for comparison and for determining the degree of inactivation in factors of powers of 10 (each power of ten reduction being referred to as one "log"). Treatments yielding no survivors were recorded as > X logs, where the ">" sign indicates no survivors, and X indicates the analytical limits of the testing.

Figure 8B:
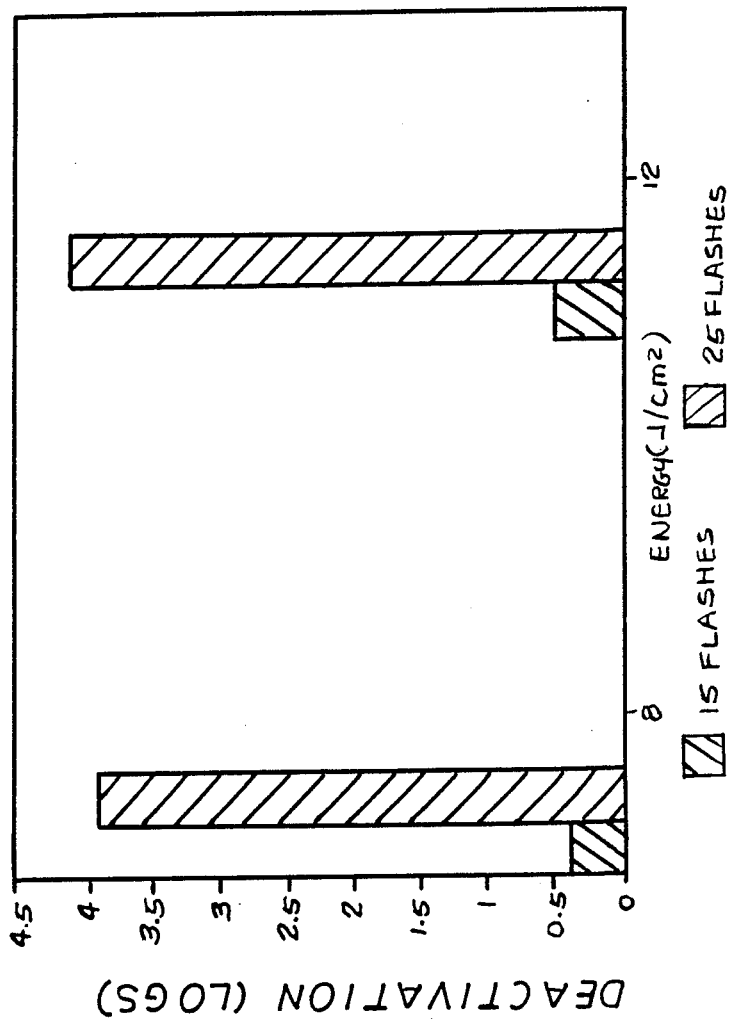
Figure 10A:
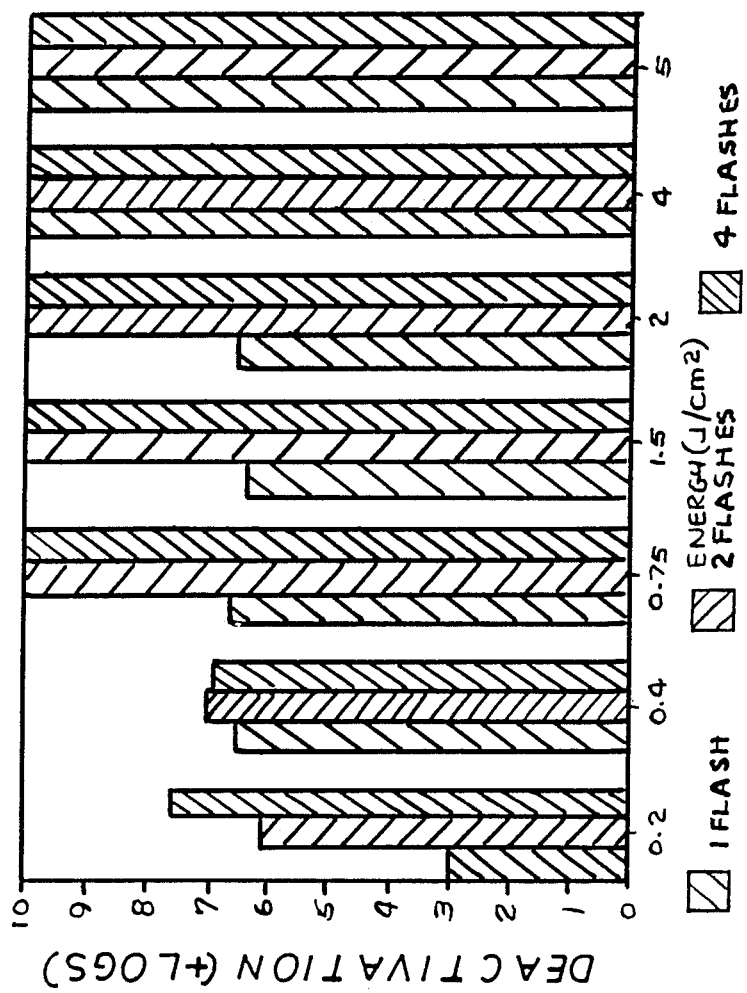
Figure 13:
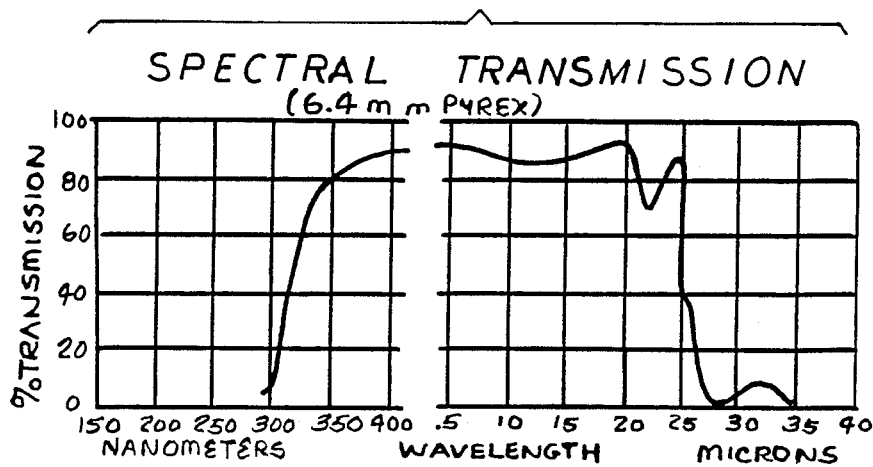
FIG. 13 is the spectral transmission curve of a glass filter adapted to remove far-UV from a pulsed flashlamp spectrum.
Figure 14:
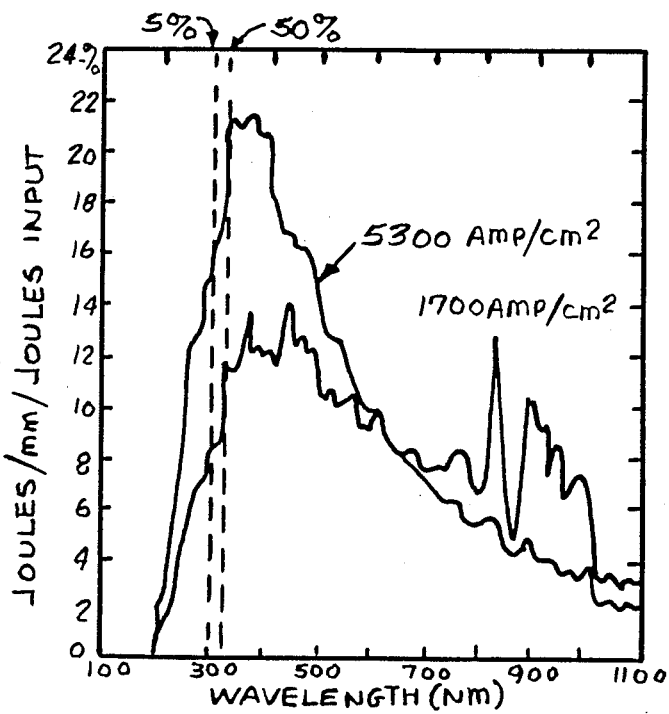
FIG. 14 is a graphic representation of the nominal spectral output of the xenon linear flashlamps of a flashlamp system with the 5% and 50% transmission wavelengths of the glass filter of FIG. 11 indicated by broken lines.

The results of the deactivation tests are given in FIGS. 7 through 12. Generally, deactivation using an unfiltered spectrum was very substantial, with complete sterilization being observed in many cases. Even at very low fluences of 0.1 J/cm² or less, several logs of deactivation were observed. When the far-UV illumination was substantially eliminated from the pulsed light spectrum through the use of a 6.4 mm (¼ inch) thick glass (Pyrex) filter, the fluence and number of flashes utilized to produce a similar deactivation effect increased substantially. The spectral transmission curve of glass UV filter is shown in FIG. 13. The nominal spectral output of Xenon linear flashlamp of the FB-300 system is shown, together with the 5 percent and 50 percent transmission wavelengths (respectively shown by dotted line) of the glass filter of FIG. 13, providing a steep transmission cutoff at about 300 nm for pulses transmitted through the glass filter. Generally at fluences of 8 to 12 J/cm², ten flashes were employed to produce greater than one log of deactivation. At these energy levels, sterilization was obtained after a larger number of flashes (from 15 to 30 depending upon the sample). Moreover, a threshold effect is apparent from the test data of FIGS. 7-17 in which a slight increase (less than 20%) in treatment intensity produced a dramatic increase in response deactivation.

EXAMPLE 7

As previously indicated, the provision of incoherent light pulses having significant far UV content substantially reduces the fluence of the light pulses which are necessary for a predetermined degree of lethal effect for treatment of a food product or package material substrate. In the absence of significant far UV content in the light pulses, absorption of the substrate (and/or microorganisms) in the near UV, visible, and near infrared wavelength range is important to provide high microorganism deactivation.

For example, in tests like those of Example 6 in which E. coli was treated with and without a glass filter for 1, 2 and 4 flashes at 1.5, 4.1, 8 and 12 J/cm², no survivors were observed on any plates treated with the full spectrum, and no effect was observed with the filter in place at these treatment levels.

It was noted, however, that the bacteriological medium used was substantially transparent to the intense incoherent illumination. Thus a 5 mm thick layer of tryptic soy agar contained in the plastic petri dishes used, attenuated the light by only about 35% and the majority of this attenuation occurred at wavelengths less than 300 mm which represented only about 15% of the total incident illumination. It was thus concluded that when the treatment spectrum was filtered by the use of the ¼ inch pyrex glass filter to remove wavelengths less than 300 nm from the light incident on the sample, the absorption of the light at the surface of the bacteriological medium was insufficient to produce efficient coupling of the light energy to the treated surface.

To demonstrate the effect of media absorptivity (and surface characteristics) on pulsed light deactivation with the Pyrex ultraviolet light filter in place, an E. coli culture was seeded on a 45 mm diameter, 0.65 micrometer pore diameter white Millipore filter and upon similar filters which had been colored black by india ink.

Seeded filters were treated in a sterile petri dish and then laid bacteria-side up on the surface of a tryptic soy agar plate. Bacteria seeded on a white millipore filter exhibited greater than 6 logs deactivation after 4 flashes at 12 J/cm². This compares to substantially no deactivation observed using bacteria seeded directly on tryptic soy agar and exposed to 4 flashes at 12 J/cm². Similarly, bacteria on a black millipore filter required only one flash at 5 J/cm² to produce greater than 6 logs deactivation.

As a further demonstration of the effect of medium absorptivity on pulsed light deactivation with the ¼ inch Pyrex glass UV filter in place, a series of experiments were performed in which nonfat dry milk or india ink were added to the bacteriological medium in order to increase its relative absorption of the intense, incoherent pulsed light. The results obtained are shown in FIG. 15-17 which illustrate the deactivation of E. coli on media containing various concentrations of nonfat dry milk (NFDM) or india ink treated with 5, 10, 15 or 20 flashes of 4 J/cm² incident illumination with the Pyrex glass filter in place.

The mechanism for deactivation using pulsed light wavelengths greater than 300 nm is believed to be different from that observed when employing spectral output including a broad far-UV spectrum. Deactivation using the full flashlamp spectrum is believed to be similar to the efforts of far-UV in dose and deactivation kinetics; deactivation using only the spectral output greater than 300 nm is believed to demonstrate a threshold relationship between dose and deactivation. This mechanism is believed to be produced by flash heating of the medium surface and varies with the ability of the uppermost layers of the medium to absorb (i.e., interact with) the incident spectral fluence during the short flash period.

Thus, two mechanisms using intense incoherent pulsed light are believed to effect microorganism inactivation, which are respectively photochemical and photothermal mechanisms. Both mechanisms may be present in effective treatment processes.

EXAMPLE 8

In order to demonstrate the deactivation of organisms within the bulk volume of a treated product, sterile 1% agar in distilled water was seeded before gelation with Staphylococcus aureus at a concentration of $10^3$ CFU per millimeter and then allowed to solidify in $15 \times 100$ mm petri plates filled to a depth greater than 10 mm. One set of plates was then treated with intense incoherent light pulses using the FB-300 system. The treated plates received 4 flashes at 6 joules per square centimeter at the agar surface while the plate was sequentially advanced across the lamp footprint to provide coverage of the entire plate. Small blocks of agar were then removed under sterile conditions from the center of control and treated plates. The blocks of agar were incubated in nutrient medium overnight at 35° C. and then compared.

Agar blocks removed from treated plates did not show any colony formation and the suspending medium remained sterile. Agar blocks removed from control plates showed extensive colony formation within the agar, growth upon the agar block surface and the suspending medium was turbid with organisms which were identified microscopically as *Staphylococci*.

These results demonstrate the ability of intense incoherent pulsed light to deactivate microbes suspended within the bulk volume of a medium if the medium is sufficiently transparent to admit the incoherent pulsed light.

EXAMPLE 9

A series of tests were peformed to determine the effectiveness of intense incoherent pulsed light for the sterilization of packaging material. The lid and cup material used by a leading U.S. food processing company for packaging a dessert pudding product were chosen as sample substrates. The cup stock material was comprised of a polyethylene/ethyl vinyl alcohol oxygen barrier plastic/polyethylene laminate. The lid stock material was comprised of an aluminum polyethylene laminate. Small pieces of each material were sterilized by autoclaving, hydrogen peroxide (3% or 10%) and heat, or UV-germicidal light; the subsequent results obtained were not affected by which pre-sterilization technique was used. One polyethylene surface of each of many samples of each material were then seeded uniformly with either *Staphylococcus aureus* in saline, *Bacillus cereus* spores in water, or *Aspergillus niger* spores in 0.1% Tergitol 7 and then air dried at 35° C. The seeding concentration was between 100 and 1000 CFU per square centimeter of surface area. Seeded pieces of lid and cup stock were then flashed with intense incoherent light using the FB-300 system. A single pulse of 1.5 millisecond (full width, half maximum) duration was given at the total light energy per square centimeter recorded. Then treated and control lid and cup stock samples were incubated individually in sterile tryptic soy broth at 35° C. for *Staphylococcus* and *Bacillus* seeded samples and room temperature (21° C.) for *Aspergillus* samples. The results obtained are recorded in Table 6 where a + (plus) indicates growth was detected and a − (minus) indicates no growth was detected after one week of incubation.

TABLE 6

| Deactivation of Vegetative and Spore Bacterial and Fungal Samples Using a Single Light Pulse | | | |
|---|---|---|---|
| Energy (Joules/cm) | Staph. Aureus | Bacillus Cereus Spores | Aspergillus Niger Spores |
| 3.0 | − | − | − |
| 2.75 | − | − | − |
| 2.50 | − | − | − |
| 2.25 | − | − | − |
| 2.0 | − | − | + |
| 1.75 | − | + | + |
| 1.5 | − | + | + |
| 1.25 | − | + | + |
| 1.0 | + | + | + |
| 0.75 | + | + | + |
| 0.5 | + | + | + |

TABLE 6-continued

| Deactivation of Vegetative and Spore Bacterial and Fungal Samples Using a Single Light Pulse | | | |
|---|---|---|---|
| Energy (Joules/cm) | Staph. Aureus | Bacillus Cereus Spores | Aspergillus Niger Spores |
| 0.25 | + | + | + |

These results demonstrate the ability of intense incoherent pulsed light to sterilize conventional polyethylene laminate packaging materials.

EXAMPLE 10

In order to demonstrate the inactivation of degradative enzymes in a solid food product by pulsed xenon flashlamp treatment to preserve the food product, a food product (potato) was selected in which enzymatic degradation is rapidly visually apparent. In this regard, freshly-cut potatoes rapidly turn brown in air through the action of the enzyme polyphenol oxidase (PPO). While the effect of the enzyme polyphenol oxidase is visually readily apparent, other enzymes may also cause deterioration of the freshness or other qualities of the food products. In these tests, potatoes were sliced, and some of the slices then treated on one surface with pulsed xenon flashlamp, while other slices were retained as control samples for comparison with the treated slices. One set of treatment conditions was to apply 5 flashes of the full spectrum of a pulsed xenon flashlamp at a fluence of 3 joules per square centimeter) 3J/cm$^2$) to the treated slice. Another set of treatment conditions was to apply two flashes of the full spectrum of the xenon flashlamp at a fluence of 3 joules per square centimeter to the treated slice. Control and treated slices were then stored in plastic petri dishes at room tempeature and observed. Within minutes, the control (untreated) potato slices begin to brown through the action of polyphenyloxidase (PPO); treated slices, however, remained white and fresh in appearance and this effect lasted during prolonged storage. It was further observed that the untreated (opposite) surfaces of the treated potato slices also turned brown, however, the degree of browning seemed to vary with slice thickness and penetration of the enzyme deactivating aspects of the light into the slice potato sample were suggested. Another potato slice was treated soon after cutting with five flashes from a pulsed xenon flashlamp at a fluence of 3 J/cm$^2$ and then held for 45 minutes under conditions identical to those used for the control specimen. This slice was cut from the same tuber as the control slice and the two slices were cut less than one minute apart. The treated potato slice was observed to be clearly fresher in appearance and suffers less from the oxidative browning action of PPO.

Similarly, a control sample is clearly discolored as compared to a like potato slice which has been treated with two high intensity short duration xenon flashlamp flashes 3 J/cm$^2$. Similar effects have been demonstrated when comparing control and treated slices of bananas and apples, which also exhibit rapid enzymatic browning of untreated slices, as compared to treated slices.

By lightly scraping a razor blade across the potato slice surface while rinsing with enzyme buffer solution, sufficient PPO enzyme was recoverable from control samples to rapidly discolor a commercial PPO assay mixture; identical scraping and rinsing of the surface of a treated potato slice surface did not rapidly discolor the PPO assay mixture. The control assay mixtures discolored due to the accumulation of the PPO endproduct, o-quinone; the treated assay mixtures remained substantially clear. This difference was rapid and long lasting; the difference between the control and treated PPO assay mixtures may be similarly demonstrated upon storage for 24 hours at room temperature in open polypropylene tubes.

A series of tests are similarly carried out to quantitatively demonstrate the effects of high intensity pulsed light treatment upon a specific enzyme system, alkaline phosphatase, which is found in various natural food products, and which may be readily measured. Alkaline phosphatase enzymes catalyze the hydrolysis of numerous phosphatase esters, such as phosphatase esters of primary and secondary alcohols and sugar alcohols. In the tests, the enzyme was diluted in buffer solution to an activity range suitable for colorimetric assay and then treated as 100 microliter droplets. Subsequently, 10 microliter aliquots of an untreated control enzyme solution or of the treated droplet solution were assayed for enzymatic activity using a kinetic colorimetric assay system, in which the enzyme is used to hydrolyze p-nitrophenyl phosphate to p-nitrophenol, which may be readily detected photometrically at an absorption wavelength of 405 nanometers. The rate of change in absorbance of 405 nm is accordingly proportional to alkaline phosphatase activity in the reaction mixture.

The data are shown in Table 7 and plotted in FIGS. 18–23. In Table 7, the treatment conditions are identified by fluence, in Joules (J) per square centimeter for each flash, and by the number of flashes (F):

TABLE 7

Effect of Flashblast Fluence and Flash Number On Enzymatic Activity of Alkaline Phosphatase

| Treatment | Measured Enzyme Activity (U/L) | |
|---|---|---|
| | Full Spectrum | Filtered Spectrum (100 gm/gal CuSO4) |
| 0 | 1229, 1185 | 1199, 1191, 1021 |
| 1J1F | 378 | |
| 2F | 52 | 646 |
| 5F | 0 | 359 |
| 10F | 0 | |
| 2J2F | 3 | 482 |
| 5F | 0 | 211 |
| 10F | 0 | |
| 3J2F | 0 | 356 |
| 5F | 0 | 104 |
| 10F | 0 | |
| 4J2F | 0 | 315 |
| 5F | 0 | 79 |
| 10F | 0 | |
| 6J2F | 0 | 208 |
| 5F | 0 | 0 |
| 10F | 0 | |

In one set of tests, treatment was carried out with a high intensity full spectrum pulsed xenon flashlamp. In a corresponding set of tests, treatment was carried out with such high intensity full spectrum pulsed xenon flashlamp light, filtered through an aqueous copper sulfate solution containing 100 grams per gallon of copper sulfate, the solution having a thickness of 0.15 centimeters. The untreated control assay mixtures were calculated to contain about 1200 enzymatic activity units per liter (3.6 U in the original 10 microliters). Treatment with a single full spectrum flash at a fluence of 1 J/cm$^2$ reduced the activity of the enzyme solution by two-thirds (activity after treatment was about one-third of the control activity). Residual activity after all other full spectrum treatments used was negligible. Treatment with pulsed xenon flashlamp light filtered through the copper sulfate solution also produced a reduction in enzyme activity; however, the filtered light was less efficient in enzyme activity reduction as compared to the effects of full spectrum xenon flashlamp light. In FIG. 22, the enzyme activity remaining after the respectively filtered or unfiltered pulsed xenon flashlamp light treatments are plotted versus the treatment dose (accumulated fluence in J/cm$^2$) used. In FIG. 23, this data is converted to show the logarithmic nature of the loss of enzyme activity with treatment. For both full spectrum flashlamp treatment flashes, and for such flashes filtered through the copper sulfate solution and copper sulfate filtered pulsed xenon flashlamp light, the dose response curve for enzyme inactivation appears linear on a semilog plot for doses of 20 J/cm$^2$ or less. Such exponential inactivation may accordingly be a "one-hit process", meaning that absorption of a single photon by a crucial target will result in inactivation. The apparent increase in enzyme deactivation efficiency for the copper sulfate filtered light treatment seen when comparing the effects at 20 J/cm$^2$ or less with those at 30 J/cm$^2$, may well result from the onset of thermal effects.

Thus, both the filtered and unfiltered pulsed xenon flashlamp light treatments appear to produce inactivation of the treated enzyme by similar photochemical mechanisms and differ largely in inactivation efficiency (the dose or number of photons required to yield a specific level of deactivation).

EXAMPLE 11

Raw shrimp, purchased at a grocery store, are peeled with surgical gloves to avoid contamination. Shrimp treated with a plurality (e.g., 4–8) flashes of a polychromatic, incoherent light from a xenon flashlamp at a fluence of 1–2 joules per square centimeter, achieved a shelf-life extension of approximately 1 week over untreated control samples. Such shelf life extension is believed to result from both enzymatic and microbiological inactivation. Similarly, shrimp seeded with *Listeria* bacteria, and chicken pieces seeded with *Salmonella* bacteria, upon such high intensity pulsed light treatment, achieve respective *Listeria* or *Salmonella* reduction by factors of 10 to 1000 or more.

This invention has wide application to the deactivation of organisms within the bulk volume of solids, liquids or gases of sufficient transmissivity to allow its efficacious and economic use, and for the deactivation of organisms upon the surface of or within the near surface region of more absorptive materials. Particular applications as described hereinabove relate to methods and apparatus for the preservation of foodstuffs, and more particularly, relate to such methods and apparatus for deactivating microorganisms on foodstuff surfaces and/or food product packaging materials. In addition, methods and apparatus in accordance with the present invention have application, for example, including, but by no means limited to: (1) the treatment of cosmetics and ingredients used in manufacturing cosmetics, (2) the treatment of equipment, products, devices or areas requiring a high degree of cleanliness, including the treatment of medical and dental instruments prior to use or prior to aseptic packaging, and the treatment of food processing equipment, to reduce the levels of contamination and the possibility of cross infection, (3) the treatment of processed or partially processed sewage effluents to reduce their organism or viral burden, (4) the treatment of water, water salt solutions, or other liquids to reduce the microbiological burden or the biological activity of the treated product, (5) the treatment of air or other gases or gaseous compounds to reduce the organism burden. The use of intense incoherent pulsed light in these and other applications for the deactivation of organisms is found to have many advantages when compared to the use of conventional continuously operating light sources or laser light sources operating in a continuous or pulsed mode. These advantages for inactivating organisms using intense incoherent pulsed sources include the provision of high fluences, the utilization of a wide spectral range, the spectral tunability available by varying the operating conditions and/or filtering, the high efficiency with which electrical energy is converted to light energy, the high product throughput made available by the use of intense pulsed sources, and the economics of operation.

While the present invention has been described with respect to certain specific embodiments, it will be appreciated that various alternatives, adaptations and modifications will become apparent from the description of the invention, which are intended to be within the scope of the following claims.

What is claimed is:

1. A method for preserving a perishable foodstuff to provide a preserved food product having improved keeping qualities with respect to deterioration resulting from microbiological surface growth or enzymatic degradation, comprising the steps of providing a solid food product to be treated, illuminating the surface of said solid food product with a first very short pulse of intense polychromatic incoherent light having a duration in the range of from about 0.001 to about 100 milliseconds, an energy density in the range of from about 0.01 to about 50 joules per square centimeter at the surface of the food product, a wavelength distribution such that at least about 70 percent of the energy of said pulse of intense polychromatic incoherent light is distributed at wavelengths between 170 nanometers and 2600 nanometers, substantially instantaneously with the duration of said first polychromatic incoherent light pulse, heating a superficial surface layer of said surface of said food product through absorption of said short intense polychromatic incoherent light pulse to a temperature effective to inactivate enzymes and microorganisms at said superficial surface layer of said solid food product before substantial thermal conduction occurs from said superficial surface layer to the interior of said food product, permitting the heat deposited in said superficial surface layer by said first very short intense pulse to dissipate from said superficial surface layer for a heat dissipation time period in the range of from about 0.001 to about 30 seconds, and illuminating the surface of said solid food product with at least one subsequent very short pulse of intense polychromatic incoherent light having a duration in the range of from about 0.001 to about 100 milliseconds, an energy density in the range of from about 0.01 to about 20 joules per square centimeter at the surface of the food product, a wavelength distribution such at least about 70 percent of the energy of said at least one subsequent pulse of intense polychromatic incoherent light is distributed at wavelengths between 170 nanometers and 2600 nanometers, substantially instantaneously with the duration of said at least one subsequent short intense polychromatic incoherent light pulse heating a superficial surface layer of said surface of said food product through absorption of said at least one subsequent short intense polychromatic incoherent light pulse to a temperature effective to inactivate enzymes or microorganisms at said superficial surface layer of said solid food product before substantial thermal conduction occurs from said superficial surface layer to the interior of said food product to provide a surface sterilized food product having improved keeping qualities.

2. A method in accordance with claim 1 wherein said pulses have a duration in the range of from about 0.001 to about 5 milliseconds, an energy density in the range of from about 0.5 to about 20 joules per square centimeter at the surface of the food product, and a wavelength distribution such that at least about 60 percent of the pulse energy is distributed at wavelengths between 300 nanometers and 2500 nanometers, and wherein a superficial surface layer of said food product is heated by at least one of said pulses to a temperature of at least 100° C.

3. A method in accordance with claim 1 wherein said energy density is in the range of from about 2 to about 20 joules per aquare centimeter, wherein said pulse duration is from about 0.01 to about 1 milliseconds and wherein said first short pulse and at least one of said subsequent pulses of polychromatic incoherent light have an energy wavelength distribution such that at least about 10 percent of their respective energy is distributed at wavelengths between 300 and 400 nanometers, and wherein said first and said subsequent pulses provide a reduction of at least a factor of 10 in the population of microorganisms at said surface of said food product.

4. A method in accordance with claim 1 wherein said food product is selected from the group consisting of solid dairy products, beef, pork, poultry, vegetables, fruits, fresh fish, and bakery goods.

5. A method according to claim 1 wherein said surface of said food product is exposed to between about 5 and about 20 of said pulses each separated by a heat dissipation time period of less than about 10 seconds.

6. A method according to claim 1, further including the step of sealing said solid food product in a transparent package prior to illuminating said surface of said solid food product through said transparent package with said first and subsequent light pulses.

7. A method according to claim 1, wherein the number of said first and subsequent light pulses is limited so as to maintain the surface temperature of said food product, ten seconds after pulsed light exposure, below about 100° C.

8. A method in accordance with claim 1 wherein said food product is contacted with an absorption enhancing agent prior to application of said light pulses.

9. A method in accordance with claim 8 wherein said light pulses each have a duration in the range of from about 0.5 to about 3 milliseconds.

10. A method for inactivating microorganisms on the surface of a packaging material or foodstuff comprising the steps of providing a packaging material of foodstuff surface to be sterilized, applying an absorption enhancing agent to said surface in sufficient amount such that at least about 10% of the incident light is absorbed within a 10 micron thick superficial layer of said surface, and illuminating said surface having said absorption enhancing agent applied thereto with at least one pulse of high intensity incoherent polychromatic light having a duration in the range of from about 0.001 to about 100 milliseconds, an energy distribution such that at least about 70% of the energy of said pulse is distributed in the wavelength range of from about 170 nanometers to about 2600 nanometers and an energy density of from about 0.01 to about 50 joules per square centimeter of said surface.

11. A method in accordance with claim 10 wherein said absorption enhancing agent is a natural food coloring.

12. A method in accordance with claim 10 wherein said absorption enhancing agent is an edible dye, and wherein said surface is illuminated with a plurality of at least 2 of said pulses, wherein the duration of said pulses is in the range of from about 0.01 to about 100 milliseconds, wherein said energy density of each of said pulses is at least about 1 joule per square centimeter of said surface and wherein at least about 70% of the energy of each of said pulses is distributed within the wavelength range of from about 170 nanometers to about 2600 nanometers.

13. A method for preserving food products, comprising the steps of applying to the entire surface of the food product a plurality of intense incoherent light pulses having a duration from about $1 \times 10^{-6}$ to $1 \times 10^{-1}$ second, an energy density in the range of from about 0.01 to 50 joules per square centimeters and a broadband wavelength distribution such that at least 70% of the light is in the wavelength range of from 170 nanometers to 2600 nanometers to inactivate enzymes and bacteria and molds at the surface and within the near surface region of the food product.

14. A method of inactivating microorganisms on a surface of a food product or packaging material comprising exposing the food product or packaging material surface to between about 1 and about 50 pulses of light spaced not more than about 10 seconds apart, the light having most of its energy distributed in the wavelength between 300 and 2500 nanometers, each pulse having a duration of between about 0.1 and about 1.0 millisecond, each pulse providing an energy density at the surface of between about 2 and about 20 joules per $cm^2$.

15. A method according to claim 14 wherein the surface is exposed to between about 5 and about 20 of said pulses.

16. A method according to claim 14 wherein said pulses are spaced between about 0.1 and about 10 seconds apart.

17. A method according to claim 14 wherein said light is incoherent and polychromatic.

18. A method according to claim 14 wherein said light is generated by a flashlamp.

19. A method according to claim 14, including sealing said food product in a transparent package prior to exposing its surfaces to said light pulses.

20. A method according to claim 14 limiting the number of said light pulses so as to maintain the measurable surface temperature of the food product or packaging material, ten seconds after pulsed light exposure, below about 130° C.

21. A method according to claim 14 wherein said material is a food product.

22. A method according to claim 14 wherein said material is a food packaging material.

23. A method for preserving a perishable foodstuff having surface enzyme activity resulting from the presence of a plurality of active enzymes, to provide a preserved food product having improved keeping qualitites, comprising the steps of
providing a solid food product to be treated having degradative enzymes at the food product surface,
illuminating the surface of said solid food product with at least one very short pulse of intense polychromatic incoherent light having a duration in the range of from about 0.001 to about 100 milliseconds, an energy density in the range of from about 0.01 to about 50 joules per square centimeter at the surface of the food product, a wavelength distribution such that at least about 70 percent of the energy of said pulse of intense polychromatic incoherent light is distributed at wavelengths between 170 nanometers and 2600 nanometers, substantially instantaneously with the duration of said first polychromatic incoherent light pulse, to substantially simultaneously reduce the activity of each of a plurality of at least two different specific enzymes to less than 75 percent of their respective initial values at the food product surface, to provide a preserved food product having increased shelf life.

24. A method in accordance with claim 23 wherein the activity of each of said plurality of enzymes is reduced to less than 10 percent of the initial activity of said respective enzyme.

25. A method in accordance with claim 23 wherein said food product is a fruit, fish, shellfish, vegetable or meat.

26. A method in accordance with claim 25 wherein said food product has a cut or bruised surface.

27. A method in accordance with claim 23 wherein said food product has microbial colony forming units on the food product surface, and wherein the number of colony forming units initially present at the food product surface is reduced by a factor of at least 10.

* * * * *

UNITED STATES PATENT AND TRADEMARK OFFICE
CERTIFICATE OF CORRECTION

PATENT NO. : 4,871,559

DATED : October 3, 1989

INVENTOR(S) : Joseph E. Dunn, et al.

It is certified that error appears in the above-identified patent and that said Letters Patent is hereby corrected as shown below:

In Column 3, line 31, change the comma "," to a semicolon --;--.

In Column 3, line 35, change the comma "," to a semicolon --;--.

In Column 3, line 42, change the comma "," to a semicolon --;--.

In Column 3, line 48, change the comma "," to a semicolon --;--.

In Column 3, line 52, change the comma "," to a semicolon --;--.

In Column 3, line 55, change the comma "," to a semicolon --;--.

In Column 3, line 61, change the comma "," to a semicolon --;--.

In Column 5, line 6, change the word "of" to the word --or--.

In Column 5, line 43, change "UV rich" to read --UV-rich--.

UNITED STATES PATENT AND TRADEMARK OFFICE
CERTIFICATE OF CORRECTION

PATENT NO. : 4,871,559

DATED : October 3, 1989

INVENTOR(S) : Joseph E. Dunn, et al.

It is certified that error appears in the above-identified patent and that said Letters Patent is hereby corrected as shown below:

In Column 5, line 47, change "UV rich" to read --UV-rich--.

In Column 7, line 43, the portion of the formula reading: (1-R) should read (1-R) where the first term in parenthesis is the numeral one.

In Column 7, line 47, change "a" to read --$\alpha$--.

In Column 7, line 47, after the word "is" insert the word --the--.

In Column 7, line 51, change the word "are" to read the word --area--.

In Column 7, line 53, the portion of the formula reading $[1-e^{-\alpha d}]$ should read $[1-e^{-\alpha d}]$ where the first term in brackets is the numeral one.

In Column 7, line 67, change the word "is" to the word --in--.

In Column 8, line 38, before the numeral "20" insert the word --about--.

In Column 9, line 31, change the word "described" to read the word --disclosed--.

In Column 9, line 34, change the word "degradation" to read the word --degradative--.

UNITED STATES PATENT AND TRADEMARK OFFICE
CERTIFICATE OF CORRECTION

PATENT NO. : 4,871,559
DATED : October 3, 1989
INVENTOR(S) : Joseph E. Dunn, et al.

It is certified that error appears in the above-identified patent and that said Letters Patent is hereby corrected as shown below:

In Column 9, line 58, change "dersired" to read the word --desired--.

In Column 11, line 2, before the word "desirably" insert the word --is--.

In Column 11, line 2, after the word "desirably" delete --be generally--.

In Column 11, line 48, after the word "as", insert the word --an--.

In Column 16, line 45, change "1.5 J/cm2" to read --1.5 J/cm$^2$--.

In Column 17, line 21, the word "Pseudomonas" should be italicized.

In Column 21, line 13, (Table 4, last line), change "1.9$_{10}$8" to read --1.9 X 10$^8$--.

In Column 22, line 53, change "inihibit" to read --inhibit--.

In Column 24, line 1, change "300 mm" to read --300 nm--.

In Column 24, line 4, change the word "pyrex" to read --Pyrex--.

In Column 24, line 63, change the word "millimeter" to read --milliliter--.

UNITED STATES PATENT AND TRADEMARK OFFICE
CERTIFICATE OF CORRECTION

PATENT NO. : 4,871,559

DATED : October 3, 1989

INVENTOR(S) : Joseph E. Dunn, et al.

It is certified that error appears in the above-identified patent and that said Letters Patent is hereby corrected as shown below:

In Column 25, line 21, change "peformed" to read the word --performed--.

In Column 25, line 29, change the words "aluminum polyethylene" to read --aluminum/polyethylene--.

In Column 26, line 22, after the word "of" delete the words --the enzyme--.

In Column 26, lines 31 and 32, change "centimeter) $3J/cm^2$)" to read --centimeter ($3J/cm^2$)--.

In Column 30, line 29, (Claim 3, line 3), change "aquare" to read --square--.

In Column 30, line 30, (Claim 3, line 4), change the numeral "0.01" to read --0.1--.

UNITED STATES PATENT AND TRADEMARK OFFICE
CERTIFICATE OF CORRECTION

PATENT NO. : 4,871,559

DATED : October 3, 1989

INVENTOR(S) : Joseph E. Dunn, et al

It is certified that error appears in the above-identified patent and that said Letters Patent is hereby corrected as shown below:

In Column 30, line 30, (Claim 3, line 4), change the word "milliseconds" to read --millisecond--.

In Column 30, line 67, (Claim 10, line 4), change the word "of" to read --or--.

Signed and Sealed this

Twenty-eighth Day of April, 1992

Attest:

HARRY F. MANBECK, JR.

Attesting Officer

Commissioner of Patents and Trademarks